(12) United States Patent
Lamps et al.

(10) Patent No.: US 11,344,398 B2
(45) Date of Patent: May 31, 2022

(54) ABDOMINAL CLOSURE METHOD AND DEVICE VARIATIONS FOR CLOSING VENTRAL HERNIAS AND REDUCING RECURRENCE

(71) Applicant: Absolutions Med, Inc., Mountain View, CA (US)

(72) Inventors: Gregory Lamps, Smyrna, GA (US); Daniel Jacobs, Mountain View, CA (US); Matthew Luis Rivera, Roswell, GA (US); Brad Richardson, Mountain View, CA (US)

(73) Assignee: Absolutions Med, Inc., Mountain View, CA (US)

(*) Notice: Subject to any disclaimer, the term of this patent is extended or adjusted under 35 U.S.C. 154(b) by 58 days.

(21) Appl. No.: 16/844,420

(22) Filed: Apr. 9, 2020

(65) Prior Publication Data

US 2020/0323614 A1    Oct. 15, 2020

Related U.S. Application Data

(60) Provisional application No. 62/925,666, filed on Oct. 24, 2019, provisional application No. 62/903,117, (Continued)

(51) Int. Cl.
*A61F 2/00* (2006.01)
*A61B 17/064* (2006.01)
*A61B 17/04* (2006.01)

(52) U.S. Cl.
CPC .......... *A61F 2/0063* (2013.01); *A61B 17/064* (2013.01); *A61B 17/0643* (2013.01);
(Continued)

(58) Field of Classification Search
CPC .............. A61B 17/0466; A61B 17/064; A61B 17/0643; A61B 17/08; A61B 2017/081; A61F 2220/0008; A61F 2220/0016
See application file for complete search history.

(56) References Cited

U.S. PATENT DOCUMENTS 363,538 A    5/1887  Penny
3,698,395 A   10/1972 Hasson
(Continued)

FOREIGN PATENT DOCUMENTS

CN    204428091 U    7/2015
CN    106901789      6/2017
(Continued)

OTHER PUBLICATIONS

Fernandez, L., "Abdominal Closure," *Medscape*, https://emedicine.medscape.com/article/1961789-technique, Jun. 14, 2019.
(Continued)

*Primary Examiner* — Todd J Scherbel
(74) *Attorney, Agent, or Firm* — Levine Bagade Han LLP

(57) ABSTRACT

A combined magnetic and bioabsorbable device for ventral hernia closure and/or tension distribution for maintenance of tissue apposition for healing, while avoiding a long-term footprint of foreign material and precluding materials spanning the interior layer of the abdominal closure where risk to visceral structures exists.

35 Claims, 32 Drawing Sheets

Related U.S. Application Data filed on Sep. 20, 2019, provisional application No. 62/840,629, filed on Apr. 30, 2019, provisional application No. 62/831,898, filed on Apr. 10, 2019.

(52) U.S. Cl.
CPC ... *A61B 17/0466* (2013.01); *A61F 2210/0004* (2013.01); *A61F 2210/009* (2013.01); *A61F 2220/005* (2013.01); *A61F 2220/0016* (2013.01)

(56) References Cited

U.S. PATENT DOCUMENTS

| | | |
|---|---|---|
| 3,926,193 A | 12/1975 | Hasson |
| 3,986,493 A | 10/1976 | Hendren |
| 4,060,089 A | 11/1977 | Noiles |
| 4,430,998 A | 2/1984 | Harvey et al. |
| 4,539,990 A | 9/1985 | Stivala |
| 4,548,202 A | 10/1985 | Duncan |
| 4,610,250 A | 9/1986 | Green |
| 4,667,674 A | 5/1987 | Korthoff et al. |
| 4,805,617 A | 2/1989 | Bedi et al. |
| 4,950,284 A | 8/1990 | Green et al. |
| 5,234,462 A | 8/1993 | Pavletic |
| 5,258,012 A | 11/1993 | Luscombe et al. |
| 5,263,971 A | 11/1993 | Hirshowitz et al. |
| 5,293,881 A | 3/1994 | Green et al. |
| 5,358,510 A | 10/1994 | Luscombe et al. |
| 5,534,010 A | 7/1996 | Peterson |
| 5,662,649 A | 9/1997 | Huebner |
| 5,800,436 A * | 9/1998 | Lerch ............... A61B 17/688 606/324 |
| 5,916,224 A | 6/1999 | Esplin |
| 6,485,503 B2 | 11/2002 | Jacobs et al. |
| 6,645,226 B1 | 11/2003 | Jacobs et al. |
| 6,730,014 B2 | 5/2004 | Wilk |
| 6,893,452 B2 | 5/2005 | Jacobs |
| 6,991,643 B2 | 1/2006 | Saadat |
| 7,156,862 B2 | 1/2007 | Jacobs et al. |
| 7,172,615 B2 | 2/2007 | Morriss et al. |
| 7,238,188 B2 * | 7/2007 | Nesper ............. A61B 17/688 606/232 |
| 7,361,185 B2 | 4/2008 | O'Malley et al. |
| 7,445,010 B2 | 11/2008 | Kugler et al. |
| 7,510,566 B2 | 3/2009 | Jacobs et al. |
| 7,972,347 B2 | 7/2011 | Garvin et al. |
| 8,114,101 B2 | 2/2012 | Criscuolo et al. |
| 8,323,313 B1 | 12/2012 | Belson et al. |
| 8,663,275 B2 | 3/2014 | O'Malley et al. |
| 8,764,778 B2 | 7/2014 | Yeretsian |
| 8,801,754 B2 | 8/2014 | Walshe |
| 8,915,942 B2 | 12/2014 | Zhang |
| 9,149,297 B2 * | 10/2015 | Kirschman ......... A61B 17/688 |
| 9,179,914 B2 | 11/2015 | Belson et al. |
| 9,198,689 B2 | 12/2015 | Dale et al. |
| 9,271,730 B2 | 3/2016 | Fleischmann |
| 9,414,840 B2 | 8/2016 | Fleischmann |
| 9,474,529 B2 | 10/2016 | Belson et al. |
| 9,486,217 B2 | 11/2016 | Moustafa |
| 9,554,799 B2 | 1/2017 | Belson et al. |
| 9,662,112 B2 | 5/2017 | Nash et al. |
| 9,693,776 B1 | 7/2017 | Moustafa |
| 10,010,710 B2 | 7/2018 | Belson et al. |
| 10,022,216 B2 | 7/2018 | Ricci et al. |
| 10,456,136 B2 | 10/2019 | Belson et al. |
| 2004/0059358 A1 | 3/2004 | Kortenbach et al. |
| 2004/0138683 A1 | 7/2004 | Shelton et al. |
| 2004/0267309 A1 | 12/2004 | Garvin |
| 2005/0197699 A1 | 9/2005 | Jacobs et al. |
| 2006/0074448 A1 | 4/2006 | Harrison et al. |
| 2006/0167482 A1 | 7/2006 | Swain et al. |
| 2006/0247637 A1 | 11/2006 | Colleran et al. |
| 2008/0046008 A1 | 2/2008 | Smith et al. |
| 2008/0262540 A1 | 10/2008 | Bangera et al. |
| 2008/0262543 A1 | 10/2008 | Bangera et al. |
| 2009/0163937 A1 | 6/2009 | Kassab et al. |
| 2009/0234358 A1 * | 9/2009 | Morales ............... A61B 17/823 606/60 |
| 2011/0092993 A1 | 4/2011 | Jacobs |
| 2012/0029539 A1 | 2/2012 | Dennis |
| 2012/0130374 A1 | 5/2012 | Bouduban et al. |
| 2012/0221044 A1 | 8/2012 | Archibald et al. |
| 2013/0325046 A1 | 12/2013 | Terwiske et al. |
| 2014/0094830 A1 | 4/2014 | Sargeant et al. |
| 2014/0214078 A1 | 7/2014 | Moustafa |
| 2014/0316323 A1 | 10/2014 | Kanevsky et al. |
| 2016/0095591 A1 * | 4/2016 | Smith ................. A61B 17/1114 606/153 |
| 2016/0113650 A1 | 4/2016 | Lord et al. |
| 2016/0310140 A1 | 10/2016 | Belson et al. |
| 2017/0156847 A1 | 6/2017 | Ricci et al. |
| 2017/0325935 A1 * | 11/2017 | Fuller ............... A61B 17/1146 |
| 2018/0078257 A1 | 3/2018 | Buttar |
| 2018/0214148 A1 | 8/2018 | Christiansen et al. |
| 2019/0038274 A1 | 2/2019 | Quintero et al. |
| 2019/0167260 A1 | 6/2019 | Levinson et al. |
| 2020/0078018 A1 | 3/2020 | Jacobs et al. |
| 2020/0107826 A1 * | 4/2020 | Kojouri ............. A61B 17/0401 |

FOREIGN PATENT DOCUMENTS

| | | |
|---|---|---|
| CN | 107822682 | 3/2018 |
| WO | WO 2017/000758 | 1/2017 |
| WO | WO 2018/031509 | 2/2018 |
| WO | WO 2018/069543 | 4/2018 |
| WO | WO 2020/055757 | 3/2020 |
| WO | WO 2020/072259 | 4/2020 |
| WO | WO 2020/210463 | 10/2020 |

OTHER PUBLICATIONS

Lorenz® Plating System LactoSorb® RapidFlap™ LS brochure, 4 pages, Oct. 1, 2008.

* cited by examiner

ABDOMINAL CLOSURE METHOD AND DEVICE VARIATIONS FOR CLOSING VENTRAL HERNIAS AND REDUCING RECURRENCE

CROSS-REFERENCE TO RELATED APPLICATIONS

This application claims the benefit of priority to U.S. Prov. App. 62/831,898 filed Apr. 10, 2019; 62/840,629 filed Apr. 30, 2019; 62/903,117 filed Sep. 20, 2019; and 62/925,666 filed Oct. 24, 2019, each of which is incorporated herein by reference in its entirety.

FIELD OF THE INVENTION

The present invention relates to devices and methods for abdominal wall surgery. More particularly, the present invention relates to apparatus and methods for closing ventral abdominal hernias without component separation, high tension closure, or mesh reinforcement, and, whether associated with hernia closure or independently, which distribute tension at a surgical closure line to aid in healing.

BACKGROUND OF THE INVENTION

There are 4 million open abdominal surgical procedures in the US (emedicine.medscape.com/article/1961789-technique). A commonly documented postoperative complication is incisional hernia resulting from the failure of structural tissue healing, which occurs in approximately 9-20% of patients after an abdominal closure. Non-surgery related ventral hernias occur as well but constitute a minority of cases. Another category of common ventral wall defect is umbilical hernias.

Abdominal surgeons are often faced with two associated problems as they relate to closure of the abdominal wall (defined herein as muscles and fascia of the anterior abdomen with or without extending to the skin or peritoneum): (1) in the case of an existing defect (hernia), optimizing the normalization of retracted abdominal wall hernia edges to their original anatomy and function; and (2) whether after normalization of retracted edges or for primary abdominal closure after laparotomy, avoiding the development of fascial dehiscence and primary or recurrent hernia.

For retracted abdominal wall edges, a marketed device that potentially restores abdominal wall anatomy to near normal is the ABRA® Abdominal Closure System (Southmedic Inc., Ontario, Canada). Through gradual dynamic tension, the edges of an abdominal wall defect are distracted back to their near-normal anatomy. However, the ABRA® device resides within the abdomen and thus presents risk of intra-abdominal visceral injury. Its position across the wound opening inhibits intra-abdominal wound management. It is furthermore indicated exclusively for patients undergoing open abdominal wound management, which are a small percentage of ventral defects compared to those with closed skin but an underlying fascial defect. In addition, the Trans Abdominal Strap (TAS Medical Inc., San Carlos, Calif., USA) utilizes a "zip tie" type ratcheting mechanism on a plastic strap to approximate abdominal wall edges. (FIG. 1). It has a segment running across the closure site both above and deep to the abdominal wall, wherein the segment deep to the abdominal wall poses a threat to underlying viscera. In addition the Trans Abdominal Strap does not provide for a dynamic closure.

In attempting to prevent primary or recurrent hernia after abdominal wall closure, options are limited for safe and effective reinforcement of the closure while the wound closure heals and develops tensile strength. Techniques generally fall into four categories: (1) closure of the wound with suture; (2) closure with mesh reinforcement; (3) bridging of the defect with mesh; and (4) component separation of abdominal wall layers with mesh reinforcement. Different forms of suture exist that add surface area to the tissue interface for added anchoring strength such as suture in the form of filamentous mesh and various barbed sutures.

Surgeons may alternatively use large retention sutures to hold the abdominal wall in position during the early post-operative phases in an attempt to prevent dehiscence. However, these sutures can also cut through tissue when under high tension. In addition, retention sutures, by design, typically have a segment running across the closure site both above and deep to the abdominal wall. The segment deep to the abdominal wall poses a threat to underlying viscera.

Mesh, the common denominator in many complex surgical approaches to abdominal wall closure, is a double-edged sword. Surgeons use mesh in various planes of the abdominal wall to reinforce closure and attempt to prevent primary or recurrent hernia formation. While essential for current techniques, mesh is associated with short- and long-term complications that are problematic for such a common product, at times with devastating consequences.

Anchoring techniques for mesh deployment create additional risks. In a manner commonly used, broadly applied mattress sutures often capture and injure a relatively large area of tissue as well as any key structure within said area such as motor nerves to abdominal musculature, potentially leading to segmental abdominal wall paralysis as well as pain.

New technologies and methodologies are desired both to normalize retracted abdominal wall hernia edges and to assist in tight abdominal closures associated either with hernia reconstruction or higher risk primary closures, all while avoiding mesh and other long term or permanent implantable components.

SUMMARY OF THE INVENTION

The ideal approach for restoring a ventral abdominal hernia to a normal anatomic state without the requirement for component separation, high tension closure, or mesh reinforcement would involve:
a. gradual dynamic distraction of tissues to their premorbid, normal position without compromise of function,
b. avoidance of loops, straps, or other device components with significant intraperitoneal segments that pose a risk to viscera,
c. limited impact on patient activity during distraction by employing wearable components,
d. allowance for easy disengagement should the need or a complication arise, and
e. in ideal circumstances, avoidance of transcutaneous components.

Embodiments are presented that meet the above criteria and allow for devices that restore near normal anatomy through magnetic distraction linked to bioabsorbable tissue anchors. Upon achievement of tissue edge apposition, the magnetic component may be removed while the bioabsorbable component remains to hold the tissue closure and optimize healing.

After restoring anatomic position of abdominal wall hernia edges, whether in primary closures or after hernia reconstruction, a component may maintain apposition of the abdominal wall fascial edges during healing while:
a. avoiding spanning materials deep to the abdominal wall (in contradistinction to retention sutures) to preclude device related injury of the underlying intestine or organs,
b. avoiding permanent mesh or other material with proclivity for complications even years after surgery,
c. avoiding resorbable mesh or other scaffolding material that may lead to a mechanically mismatched scar layer,
d. allowing easy deployment,
e. distributing tension across as many points and across the widest area practically and safely allowed, and
f. gradually transferring forces from the anchoring device to the healing scar.

One form of the embodiment used after tissue edge apposition includes bioabsorbable components that maintain tissue closure and optimize healing. For the bioabsorbable components, mechanisms are utilized to form a connection between the posterior (interior of abdominal wall) and anterior (exterior of abdominal wall) elements. These mechanisms may include various fastening mechanisms, e.g., threaded features, ratchet features, threaded features, etc. used in conjunction with securement mechanisms, e.g., ratchets. In addition, various mechanisms are described for the attachment of components to each other across the wound. These mechanisms include ratcheting straps, ball chains, perforated strips, etc.

In one variation of a tissue anchoring assembly, the assembly may generally comprise a first member having one or more first piercing elements extending from a first surface configured for contact against a first tissue region and a second member having one or more second piercing elements extending from a second surface configured for contact against a second tissue region, wherein the second member defines one or more openings corresponding to a position of the one or more first piercing elements, and wherein the first member and second member are configured to be secured relative to one another via the one or more first piercing elements.

In one method of approximating tissue, the method may generally comprise attaching a first tissue anchoring assembly to a first region of tissue, wherein the first tissue anchoring assembly comprises a platform or base having one or more first piercing elements extending from a first surface. The method may further include attaching a second tissue anchoring assembly to a second region of tissue to be apposed to the first region of tissue, wherein the second tissue anchoring assembly comprises a second platform or base having one or more second piercing elements extending from a second surface, and approximating the first region of tissue towards the second region of tissue by adjusting a connecting element secured to the first tissue anchoring assembly and the second tissue anchoring assembly.

Another variation of the tissue anchor apparatus may generally comprise a first member defining one or more anchoring members having a length extending from a surface of the first member, each of the one or more anchoring members having a terminal piercing end and having features over at least a portion of the length and a second member defining one or more openings through which the anchoring members are received in a corresponding manner. The apparatus may further include a third member defining one or more openings through which the anchoring members are received, wherein the third member is configured to be secured in position relative to the anchoring members and maintain a position of the second member relative to the first member.

Yet another variation of a tissue anchoring assembly may generally comprise a first member having one or more first piercing elements extending from a first surface configured for contact against a first tissue region and a second member configured for contact against a second tissue region, wherein the second member defines one or more openings corresponding to a position of the one or more first piercing elements, and wherein the first member and second member are configured to be secured relative to one another via the one or more first piercing elements. The assembly may further comprise a magnetically attractive element attachable to the first member and/or the second member.

DETAILED DESCRIPTION OF THE INVENTION

Figure 1:
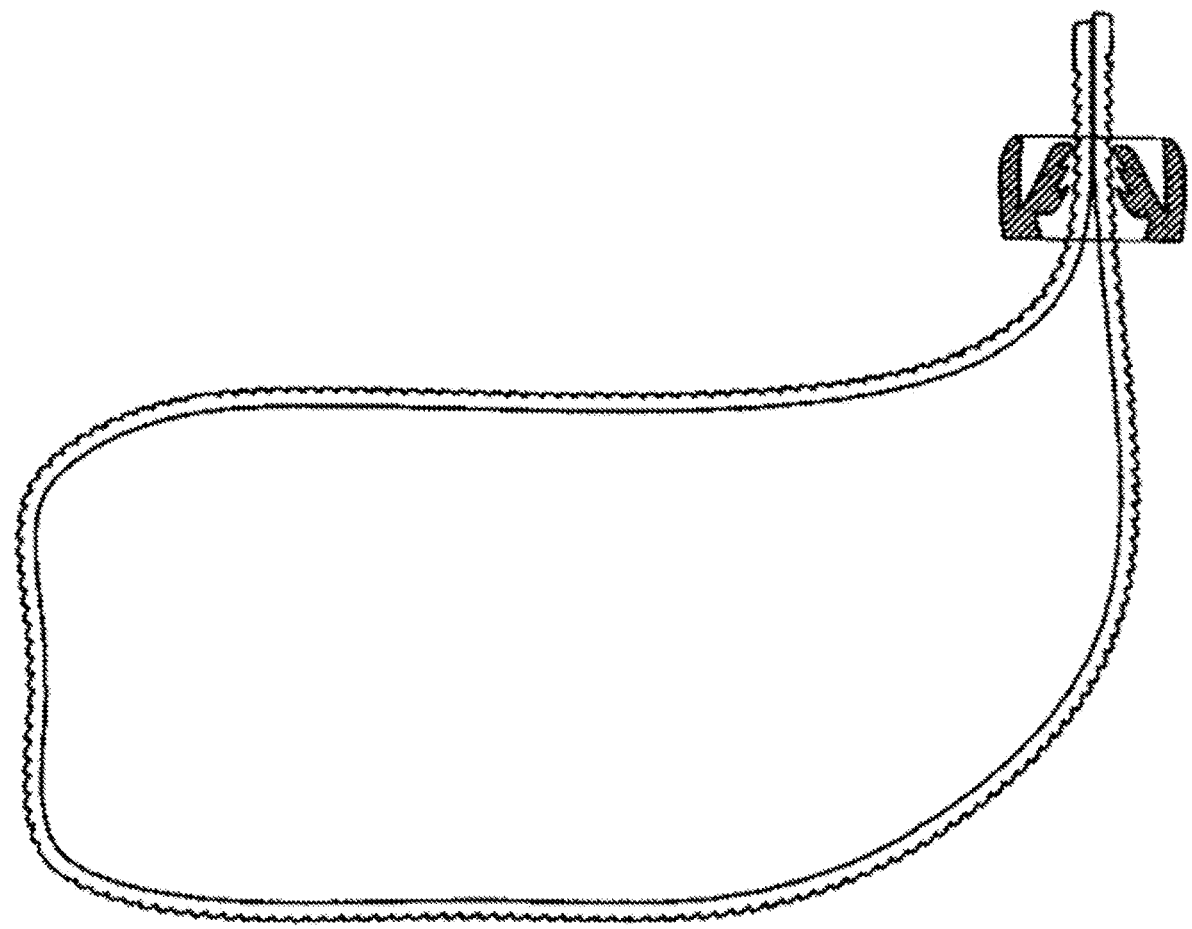
FIG. 1 shows a cross-section view of a conventional device for approximating abdominal wall hernia edges.
Figure 2:
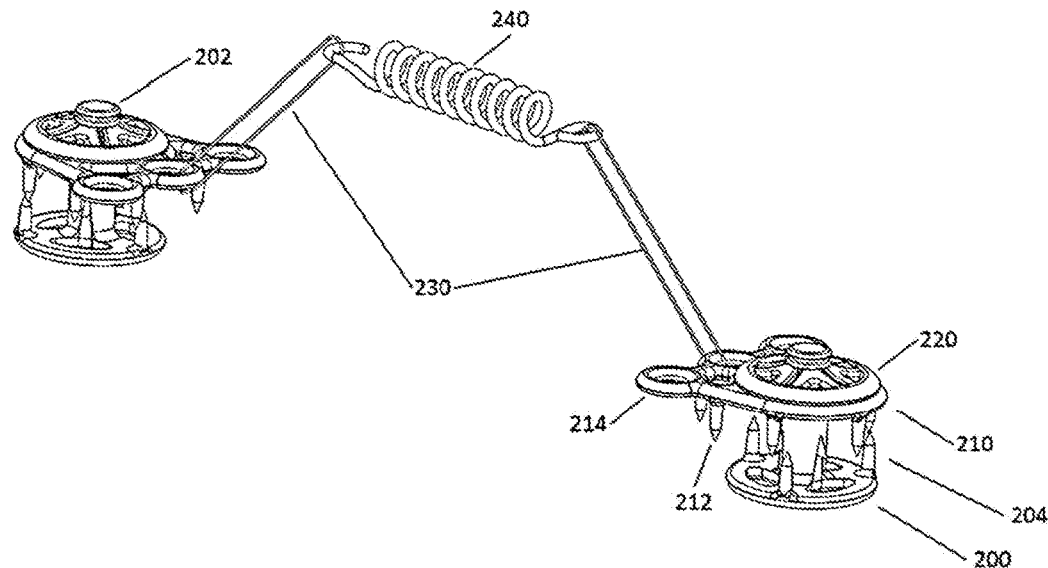
FIG. 2 shows a perspective view of a pair of anchors with a percutaneous member used to approximate the devices after initial implantation.

For the purpose of restoring abdominal anatomy to normal, or near normal, in closing a ventral hernia defect, one method utilizes soft-tissue anchors 202, 220 (described in further detail below) and extends a flexible connecting member 230 from each anchor percutaneously. The anchors 202, 220 may be secured to the underlying abdominal wall while the connecting member 230 may extend percutaneously through the tissue from the implanted anchors 202, 220 to external of the skin of the patient. This percutaneous connecting member 230 may be a suture or other structure which can be retied periodically or otherwise have force applied to it to bring the anchors towards each other (FIG. 2). The terminal ends or looped portion of the connecting members 230 may be coupled to one another via a biasing member 240 such that the biasing member 240 and distal portion of each opposed connecting member 230 remain external to the patient. This may include having the percutaneous connecting members 230 pulled towards each other with a biasing member 240 such as a spring, elastic band, mechanical system, or other mechanism for applying a biasing force. Typically, the force applied by the biasing member 240 will be in the range of, e.g., 1 N to 8 N, with the force preferably held to below, e.g., 4 N. Connecting members 230 can be configured to be of sufficient length to extend from the anchor through the surface of the skin, this length may be highly dependent on the specific anatomy of the individual patient. The biasing member 240 in an extended length should be long enough to span the distance between connecting members 230, for most patients this should be less than, e.g., 30 cm. Once the margins of the abdominal wall have been sufficiently approximated to within, e.g., 3 cm or ideally less than 1 cm, biasing member 240 and the percutaneous connecting members 230 may be removed, and the anchors 202, 220 may be connected directly to one another with suture or other means subcutaneously.

Figure 3:
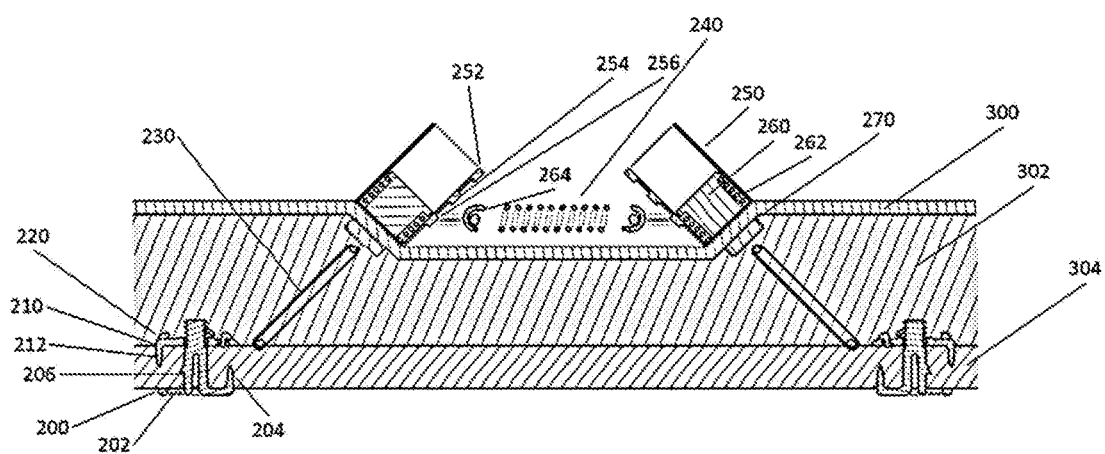
FIG. 3 shows a cross-section of a pair of abdominal wall anchors with connected magnets or magnetic material implanted below the skin (subcutaneous) and electromagnets exterior to the skin with an interconnecting biasing member.

In a different embodiment, a magnetic plate or component 270 may be integral to, or attached directly to, an intervening connecting segment 230 to the soft-tissue anchor secured to the underlying abdominal wall. Rigid or semi-rigid attachment between the connecting segment 230 and component 270 may be achieved by insert molding, adhesives, or other methods such as heat staking, ultrasonic welding, press fit, snaps, etc. Alternatively, a more compliant attachment may be achieved through use of a suture or other flexible member which is attached to the soft-tissue anchor and magnetic component. Preferably the magnetic component 270 is positioned such that it is superficial to the subcutaneous adipose tissue 302 and just below skin 300 (FIG. 3). The attachment method may allow for adjustment of the distance between the magnetic member and the soft-tissue anchor to allow the magnetic piece to be positioned in the desired layer of the tissues while remaining subcutaneous. In this manner, the magnetic component 270, anchors, and connecting segments 230 may remain subcutaneously positioned within the patient. The magnetic component(s) may comprise a ferrous magnetic material or a material in which magnetism can be induced (for example a steel plate).

In another variation, the magnetic component(s) may be a permanent magnet(s). Alternatively, the magnetic component(s) could comprise an electromagnet(s). However this leads to additional complexity in the system due to the requirement to provide electric current through the skin (either wireless or through percutaneous wires). The magnetic component(s) may be encapsulated in another material such as a plastic to improve the biocompatibility of the device and/or avoid corrosion of the magnet. In another embodiment, the attachment may comprise a suture or wire passed through holes or otherwise around all or a portion of the posterior portion of the soft tissue anchor, through the abdominal wall, through holes in the anterior components of the soft-tissue anchor or otherwise around all of a portion of said components, and then is connected to the magnetic component.

On the exterior of the body, external magnets 260 (FIG. 3) corresponding to the implanted magnetic components 270 may be positioned to attract the magnetic component 270 under the abdominal skin. These external magnets 260 may have a biasing mechanism 240 to pull the units on opposite sides of the wound, incision, or hernia towards each other, thereby pulling the respective sub-dermal magnetic components 270 closer to each other, and ultimately the edges of the abdominal wall on each side of the wound defect towards each other. The external magnets 260 may apply a force ranging from, e.g., 1 N to 8 N. The exterior magnets 260 may comprise permanent magnets or electromagnets such that in the case of electromagnets the forces between the exterior magnets 260 and the interior magnets 270 can be limited, controlled, and/or cycled. Specifically, due to the risk of tissue necrosis, the pressure exerted on any tissues between the exterior magnets 260 and the interior magnets 270 can be maintained at, e.g., 32 mmHg (0.619 psi, 4.27 kPa) or less. At pressures exceeding this level, the perfusion of blood to the tissues may be impeded and if this situation is maintained for extended periods of time, necrosis or compromise of the tissue may occur. Alternatively, the forces applied by the external magnets 260 can be varied in such a way that the pressure exerted on the tissues exceeds, e.g., 32 mmHg, for periods of time but drops down to levels lower than 32 mmHg at other time periods to allow sufficient intermittent perfusion of the tissues to maintain tissue health.

Figure 4:
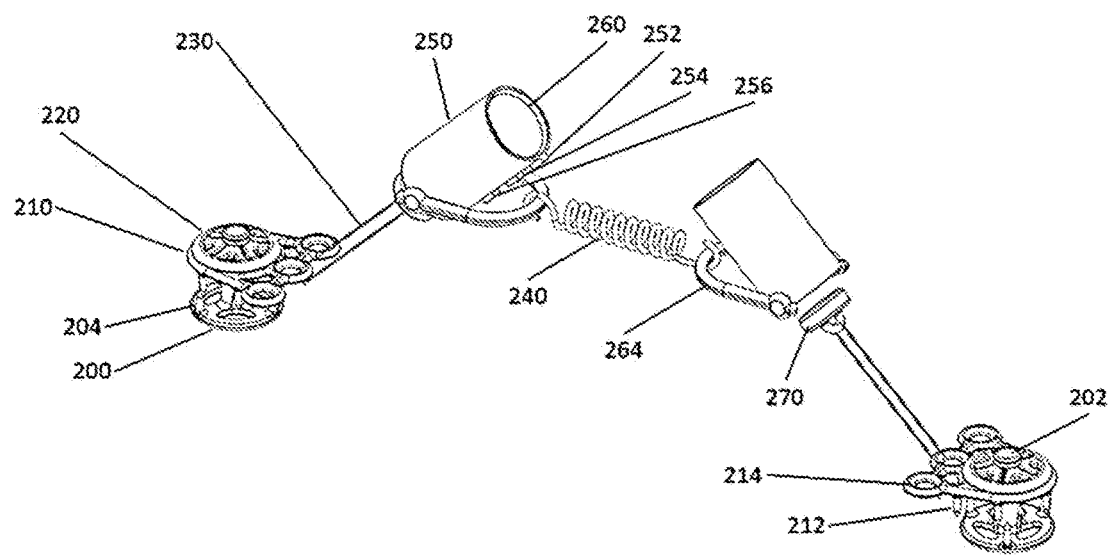
FIG. 4 shows a perspective view of a pair of abdominal wall anchors connected to subcutaneous magnets or magnetic material and external magnets connected by a biasing member to pull in a medial direction.

The mechanism (FIG. 4) to pull the exterior magnets 260 towards each other (and thereby move the subcutaneous magnetic material 270 towards each other, approximating the margins of the abdominal wall) may comprise a biasing member 240 which applies a known force, an electro-mechanical driving unit capable of applying a known force, or other mechanism which is capable of moving the exterior magnets closer to each other. In the case of an elastic member (FIG. 4), the system may comprise elastic bands, constant force springs, torsion springs, coil springs, or other similar elements. The electro-mechanical system may comprise a servomotor, stepper motor, linear actuator, or other motor coupled directly or indirectly to the magnets. Force may also be produced through pneumatic, hydraulic, or combustion systems. Mechanisms such as a rack-and-pinion can be used to translate rotary motion into linear motion. A mechanism comprised of multiple gears can be envisioned to cause the desired motion. Alternatively, a system of cables and pulleys can be used to move the external magnets. Any number of other mechanisms may be used as well.

In utilizing magnets (in this case, one subcutaneous and one external), the force of magnetic attraction (or repulsion) between two magnets varies depending upon the distance between the magnets. Although the ratio in which the force changes depends upon the distance between and the geometry of the magnets, at intermediate distances it typically changes proportional to the inverse square of the distance (a magnet twice as far away pulls with one quarter the force). For example, magnets that are sized to provide a certain force through 10 mm of intervening tissue would create 4 times that force when only 5 mm of tissue is present. This force ratio is the same whether there are two magnets or one magnet and one component in which magnetism can be temporarily induced.

The internal magnet 270 of the device may either be placed on the fascia of the abdominal wall 304 (leaving the subcutaneous fat and skin between the magnet and the plate) or superficial to the subcutaneous fat 302, leaving only the relatively thin skin 300 between the plates and the magnets (FIG. 3). In either case, but especially in the case of having subcutaneous fat increasing the separation of the plate 270 and the magnet 260, any variation in tissue thickness can radically change the amount of force (and pressure) applied by the magnets to the tissues. For example, if the magnets are sized such that 10 mm of tissue results in the desired pressure less than 4.27 kPa, but the actual tissue is only 5 mm thick, then the pressure could rise to 8.54 kPa leading to serious necrosis. For these reasons the interior magnetic element 270 may be placed in one variation beneath the skin but preferably not below the subcutaneous fat.

Figure 5:
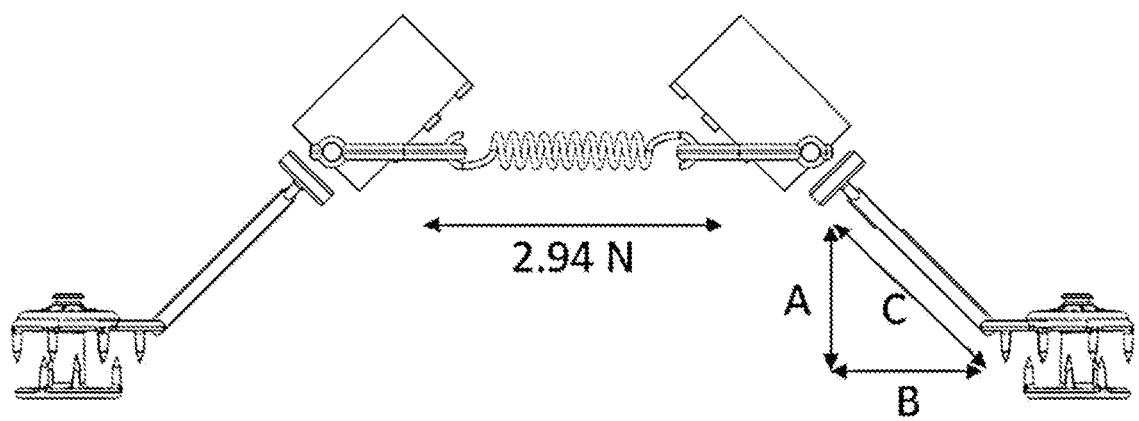
FIG. 5 illustrates an example showing approximate vectors of forces on magnets and anchors of FIG. 4.

For the case of approximating edges of the abdominal wall, a force applied to the tissue may be less than, e.g., 400 g, and possibly less than, e.g., 300 g (2.94 N) per pull point. The exterior magnets 260 are located in a different plane than the abdominal wall, and therefore tend to pull on the interior components at an angle, creating a force vector (FIG. 5). In order to transfer a medial pulling force of 2.94 N (for example), the exterior magnets 260 may be pulled toward each other with a similar force. In the example of a 45-degree angle of the connecting member 230 in FIG. 5, A and B both equal the 2.94 N apposition force that is being applied in the exterior plane. This creates a resultant vector (C) between the exterior magnet 260 and the interior magnet 270 which is equal to $C=2.94N*\sqrt{2}=4.15$ N. Distributing the 4.15 N force across the tissues and maintaining the pressure below 4.27 kPa requires an area greater than 9.75 cm$^2$. This is the area of a circle with a diameter greater than 3.5 cm. Alternatively, as described below, an intermittent magnetic force would protect tissue while allowing a smaller diameter circle. While this example is specific to one particular variation, other configurations may be utilized to generate a similar effect.

In order to limit the forces (pressure) applied to the tissues, at least a portion of the magnetic force may be provided by an electromagnet. If one or more electromagnets are utilized, force can be controlled by either turning off an electromagnet, limiting the current in the wire of the electromagnet, rapidly cycling the electromagnet on and off (pulse width modulation or similar switching), or reversing the polarity of an electromagnet (creating a repulsive force relative to another electromagnet or permanent magnet). In any of these cases, in order to control the force of the magnets, it is necessary to measure or limit the forces. Alternatively, if well characterized magnets are used, knowing the magnetic field strength at a reference point in the system, the distance between the magnets can be determined. Therefore, the following control methodologies may be implemented:

If it is desired to measure magnetic field strength, a flux gate or similar sensor capable of measuring magnetic field strength can be placed between the two magnets (or between a magnet and a material with induced magnetism). By knowing the level of magnetism of the magnets, the strength of the magnetic field at a point between the two magnets can be used to determine the distance between the magnets. This methodology is dependent on knowing the magnetic strength of both magnets, having a well calibrated sensor, and limiting external magnetic fields (interference). The strength of the magnetic field at the location of the sensor could then be utilized to modulate the power delivered to the electromagnet and limit the magnetic force, thereby controlling the pressure applied to the tissues between the magnets.

An alternate method to control the pressure applied to the tissues between the magnetic components is to either directly measure the force acting on one of the components (through use of a load cell or similar sensor) or to measure the distance an elastic member (with a known deflection rate) such as a spring is deflected. The distance can then be converted into force and the power to the electromagnet varied to control the force. Various mechanisms for measuring distance include: linear potentiometer, rotary potentiometer (with a mechanism to change linear displacement into rotation), linear encoder (glass scale or other), rotary encoder (with a mechanism to change linear displacement into rotation), optical displacement measurement (laser, diffraction, or image processing), capacitive sensor, magnetic sensor, inductive sensor, eddy current sensor, or other known methods of measuring displacement. Another method to control the force (and therefore) pressure applied to the skin between two magnets is to use one or more switches 252, 254, 256 that are activated when a specific force is applied to the magnet, thereby displacing the magnet 260 acting against a biasing member 262 (e.g., a spring) of known spring rate. The switch may turn the electromagnet off until the force drops below a safe level. Multiple switches (e.g., two or more) can be used to create a stepped effect where the one switch reduces the electromagnetic force and a second switch turns off the electromagnet. Electronic circuitry can be utilized to perform signal processing. For example, slowing the reaction time of the electromagnet current limits spurious switching of the electromagnet due to movement of the patient or other vibration that creates a momentary increase of force, but which is insufficient in duration to lead to necrosis or other undesirable effects. Alternately, the switch or switches logic can be reversed such that one or more switches increases the current through the electromagnet if the displacement is insufficient. Any number of different switch types may be used, e.g., optical switches, mechanical switches, various electrical contacts, photoresistor/diode pairs, etc.

Figure 6:
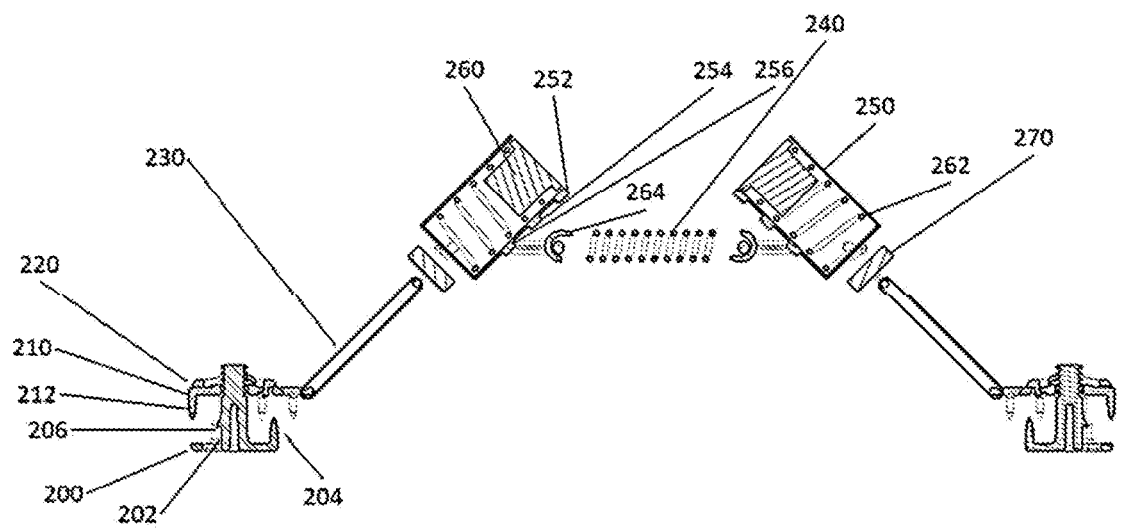
FIG. 6 shows a cross-section of an electromagnet in a housing with biasing members, such as a spring, and switches to provide feedback and control of magnet position. Electromagnet may be located activating a first switch.
Figure 7:
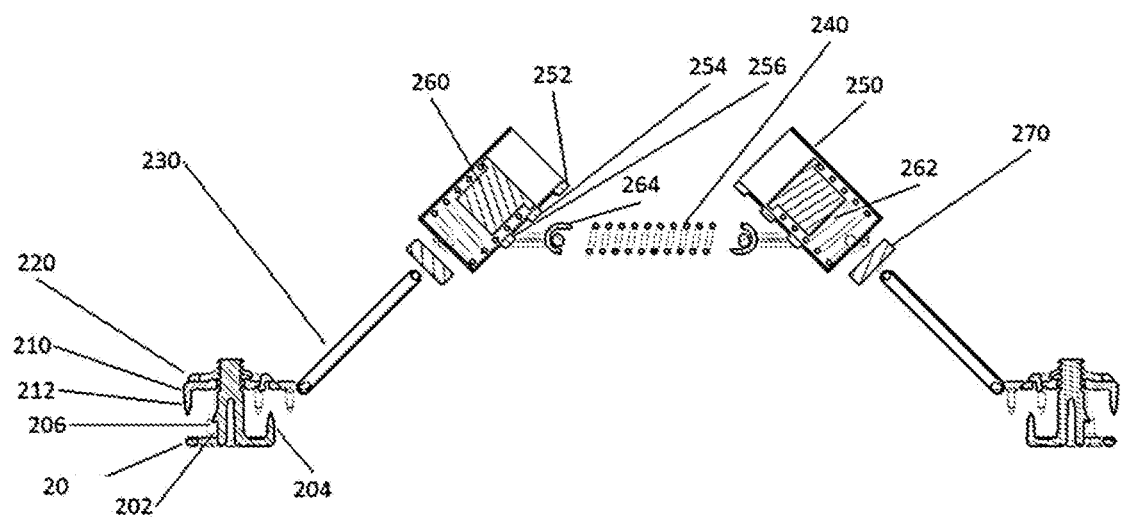
FIG. 7 shows a cross section of an electromagnet in a housing with biasing member and switches to provide feedback and control of magnet position. Electromagnet may be located activating a second switch.
Figure 8:
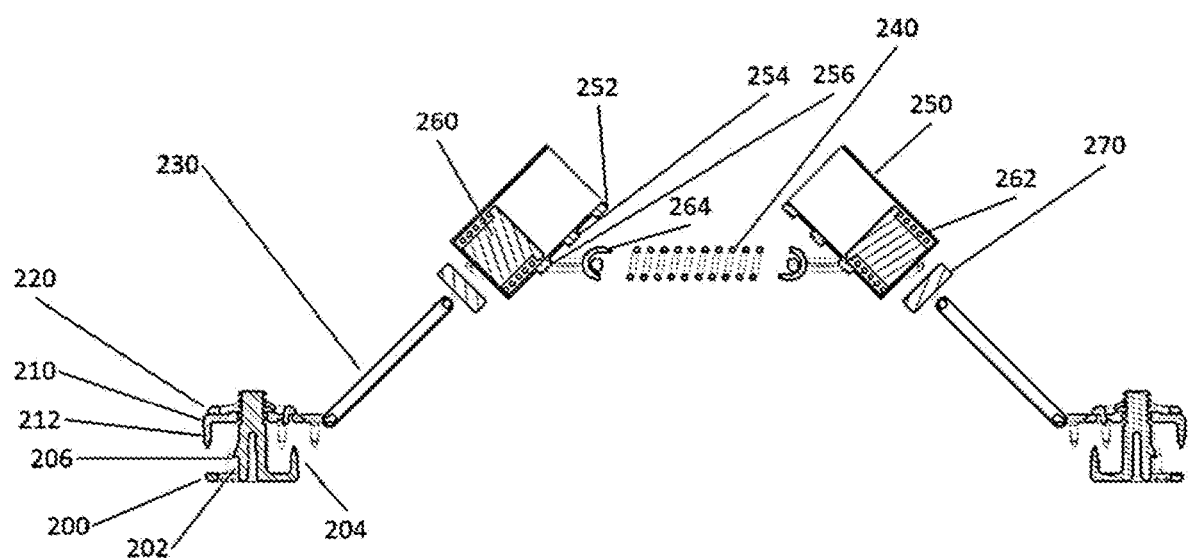
FIG. 8 shows a cross section of an electromagnet in a housing with biasing member and switches to provide feedback and control of magnet position. Electromagnet may be located activating a third switch.

FIGS. 6, 7, and 8 show cross-sectional views of an electromagnet 260 held within a housing 250. The electromagnet 260 may be slidingly retained within the housing 250 while being held off the bottom of the housing 250 and away from the internal magnet 270, e.g., by a spring 262 of known rate (force) or other biasing mechanism. When attraction between the electromagnet 260 and the internal magnet 270 is sufficient for the electromagnet 260 to change the state of a switch (e.g., turns 'on'), the electromagnet 260 may be turned off until the switch turns 'off'. If additional switches, e.g., switches 252, 254, 256 are used in combination with multiple separate windings on the same electromagnet core (or separate cores), then the force of the electromagnet 260 can be modulated stepwise by switching on one or more of the windings at a time. Alternatively, the plurality of switches 252, 254, 256 can be utilized in conjunction with a method of limiting current or voltage in the electromagnet windings thereby limiting the electromagnetic force depending on the position of the electromagnet in the housing.

Figure 9:
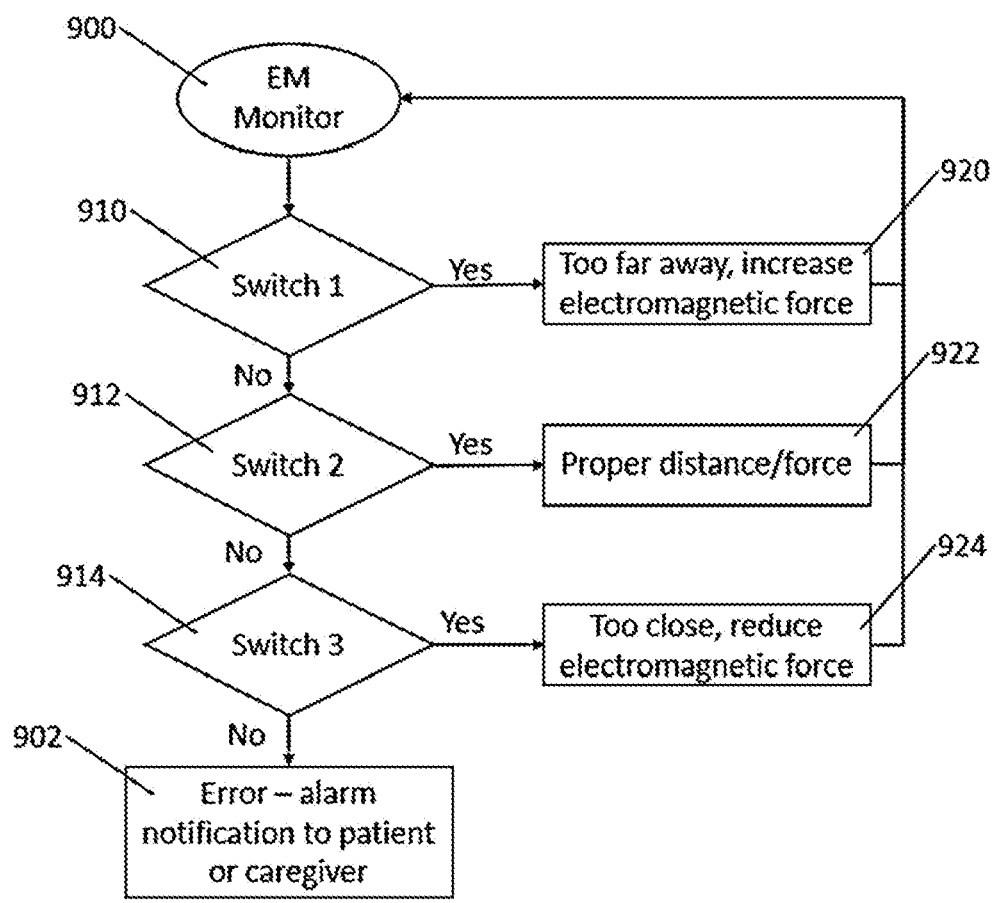
FIG. 9 shows a logic map for controlling electromagnets based on switch states.

One possible decision tree (logic) for control based on position of the electromagnet as detected by three switches is illustrated in FIG. 9. In this embodiment, the control system continually or cyclically monitors the state of the switches 252, 254, 256 starting the at beginning of the logic 900. If the electromagnet is detected activating the first switch 252 (step 910), then the system increases the voltage to the electromagnet to increase the electromagnetic force 920. If the electromagnet is not detected activating the first switch 252, 910, then the system checks the state of the second switch 254 (step 912). If the electromagnet is detected activating the second switch 254 (step 912), then the system maintains a constant voltage to the electromagnet to maintain a constant electromagnetic force 922. If the electromagnet is not detected activating the second switch 254 (step 912), then the system checks the state of the third switch 256 (step 914). If the electromagnet is detected activating the third switch 256 (step 914), then the system decreases the voltage to the electromagnet to maintain a decrease the electromagnetic force 924. After adjusting the electromagnetic force in steps 920, 922, 924, the logic loops and repeats the query of the plurality of switches. If the electromagnet is not detected activating any of the switches 252, 254, 256 (steps 910, 912, 914), then the logic stops and an error message is presented to the user 902.

Figure 10:
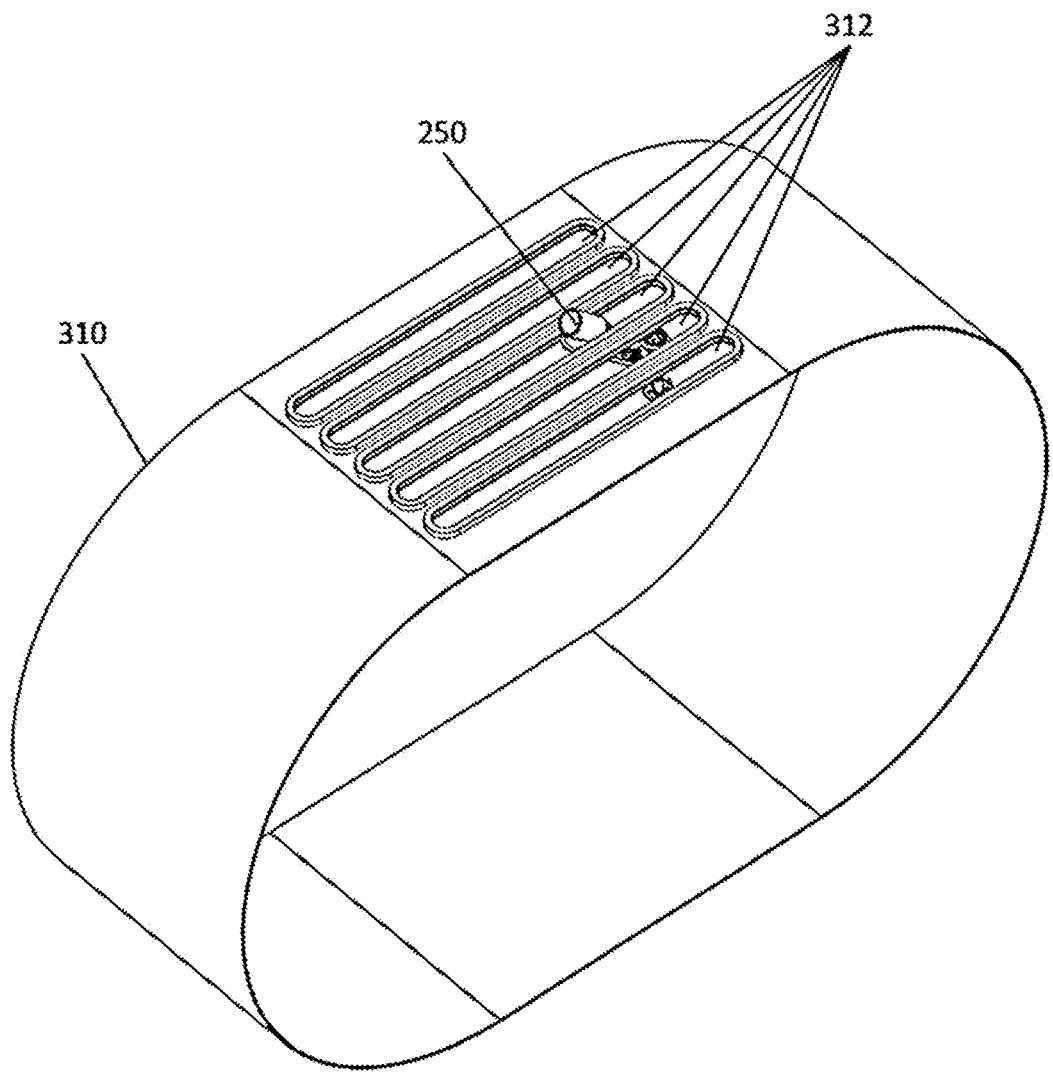
FIG. 10 shows a perspective view of an abdominal binder with tracks.

In another version, the external magnetic pieces are held against the skin by a binder 310. The binder 310 may be comprised of a flexible fabric such as cloth which allows for the binder 310 to be wrapped around the body of the patient. The binder 310 may include biasing components to apply gentle, dynamic pressure. In one variation (shown in the perspective view of FIG. 10), slits, grooves, or tracks 312 may be provided in the binder 310 such that the tracks 312 are aligned in parallel with one another across the width of the binder 310. These tracks 312 may be positioned over the patient body such that the tracks 312 extend across and over the abdominal wall defect to provide a channel through which the magnetic components 250 may be retained in a slidable manner in order to help maintain the orientation and positioning of the components relative to one another. Such an arrangement can also be used to prevent unintentional decoupling of the external magnetic pieces from the internal pieces. This is especially true in the case of ambulatory patients where daily movements may induce an acceleration on the external pieces tending to overcome the magnetic attraction forces to the internal pieces and causing detachment of the external magnets from the patient. In addition, the tracks can serve the additional purpose of further constraining the motion of device pairs relative to other device pairs located elsewhere along the abdominal wall defect.

Various magnetic shielding covers may be included to place over the dynamic system to prevent problems with unwanted external magnetic attraction. Materials might include metals such as iron, steel, nickel, and cobalt (or their alloys) or other ferromagnetic materials. More specialized materials that may be considered are specialized and made specifically for magnetic shielding such as MuMetal® (Milspec 14411C, Magnetic Shield Corp., Bensenville, Ill.).

Tools may also be included to allow easy passage of the internal magnets either from an open wound to the desired position or from outside the skin to the desired subcutaneous position.

The above electronic system may incorporate Wi-Fi, Bluetooth® (Bluetooth Sig, Inc., Kirkland, Wash.) or other provisions for connection to a network or external computing device to allow for tracking and control of force, movement of the tissues, and/or other metrics via an application (app), internet connection, remote monitoring, or integration in the Internet of Things (IoT), etc. This may allow control and/or monitoring by the patient, a caregiver, a medical professional, or automated algorithm (including 'artificial intelligence').

Once edges of an abdominal wall defect are brought together via the devices and methods described herein, or separately at the completion of a primary abdominal procedure, a tissue anchor is described that attaches to abdominal wall soft tissue edges (or near the edges) and allows for the application of distributed tensile force across said soft tissues. The devices and methods described herein may be used in combination with any of the devices and methods incorporated, and features described may be used in combination with the devices and methods described herein in any combination.

The embodiments for the soft tissue anchor described may be made partially or entirely from bioabsorbable (bioresorbable) materials. Bioabsorbable materials may include, but are not limited to, polylactic acid (PLA), polyglycolic acid (PGA), lactic/glycolic acid copolymers (PLGA), polydioxanone (PDO, PDS), trimethylene carbonate (TMC), and polycaprolactone (PCL). Also included in this bioresorbable materials are the various co-polymers of these materials such as PLA-co-TMC or PLGA-co-PDO.

Alternatively, the devices may be made partially or entirely from materials that are not bioabsorbable. Non-bioabsorbable materials could include stainless steel, titanium, polyethylene (PE), polypropylene (PP), polyetheretherketone (PEEK), polyphenylene sulfide (PPS), or other materials which do not significantly degrade in the body.

The various embodiments may have antibiotics, active pharmaceuticals, and/or antimicrobials as a surface coating or incorporated into the material.

The prongs and tines described below may have any of a variety of geometries. These include, but are not limited to, cylindrical shaped, oval, rectilinear, conic, parabolic, or other shapes. The tips of the prongs and tines can also take multiple forms such a cutting, atraumatic, traumatic, multibevel, 'pencil' tip, etc.

The portion of the anchor that passes through the abdominal wall fascia and muscle may be angled or hinged relative to the base or platform to allow the medial forces of the suture to align more in parallel with the anchoring component, thus reducing an anterior moment arm that would tend to apply all or most of the force at the anterior rectus sheath rather than across the entire abdominal wall thickness (anterior rectus sheath, rectus muscle, posterior rectus sheath where present).

Figure 11:
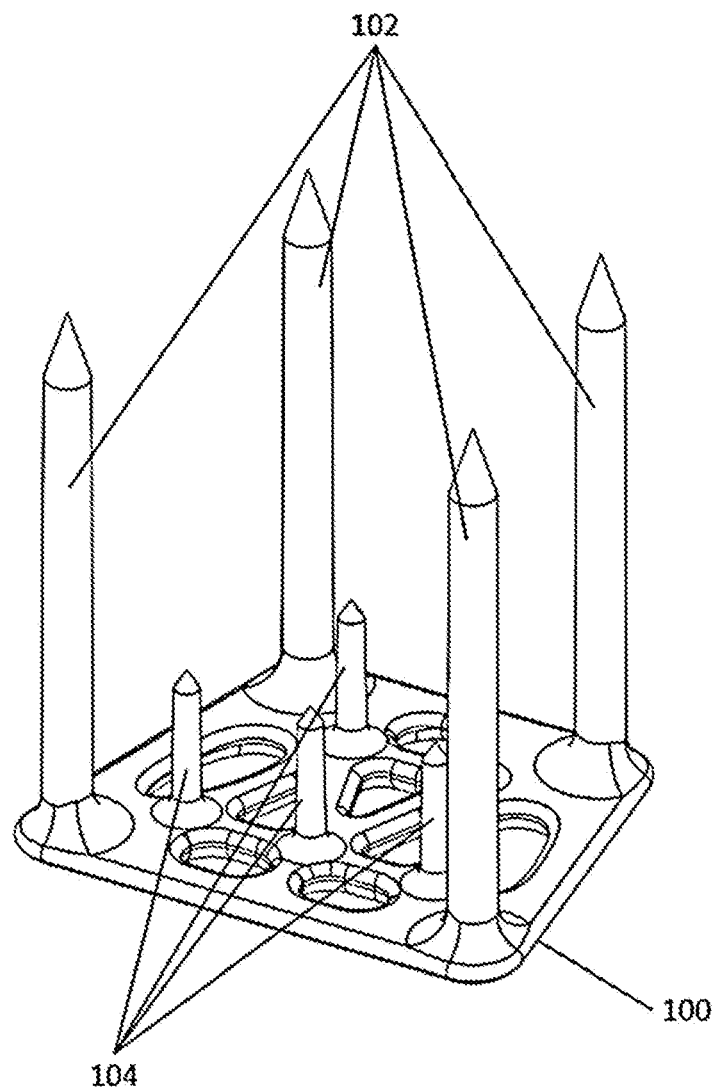
FIG. 11 shows a perspective view of an anchor with, e.g., four prongs, and one or more tines.

In one embodiment (perspective view of FIG. 11), an anchor 100, having a base or platform, has one or more prongs 102 which penetrate through the anterior rectus sheath (fascia) where tensile strength is greatest, and/or tines 104 intended to penetrate only the posterior rectus sheath (fascia) to the extent that it is present. The anchor 100 may comprise a base defining one or more openings therethrough with prongs 102 that may project away from the base either in a normal direction or angled relative to a plane defined by the base. The prongs 102 may also define a first diameter or thickness, e.g., 1 to 6 mm, and may also define any number of cross-sectional shapes, as described herein above. Additionally, the prongs 102 may extend at a distance of, e.g., 7 to 25 mm (although longer lengths may be needed for unusually thick abdominal walls), to help ensure that the prongs 102 can extend through the entire thickness of the abdominal wall to which the anchor 100 is to be secured. Excess portions of the lengths may be removed as described in further detail herein.

The prongs 102 may also be positioned over the base to provide a stable securement relative to the tissue to which they are attached. The example shown illustrates four prongs 102 extending in parallel from each respective corner of the base but other variations may utilize fewer or greater numbers of prongs 102 which may be positioned at alternate locations of the base.

The tines 104 may also be incorporated to extend from the base such that they each define a second diameter or thickness, e.g., 1 to 6 mm, and may also define any number of cross-sectional shapes, as described hereinabove. Additionally, the tines 104 may extend at a relatively shorter distance of, e.g., 1 to 8 mm, than the prongs 102 to help ensure further engagement with the tissue but may not extend through the entire width of the tissue. Furthermore, the tines 104 may be positioned over the base and in-between the prongs 102, as shown.

In another embodiment, the anchor may comprise a base or platform with prongs, and at least two components (holes in the prongs) that pass through the abdominal wall to allow for a loop of suture to pass. The holes may be parallel to the innervation (nearly horizontal or axial) to avoid catching key nerve structures within the suture loop. The suture anchor is inserted from the interior of the abdominal wall with the prongs extending partially or completely through the abdominal wall. A suture can then be passed through the hole(s) and connect the suture anchors on each side of the incision to one another, thus holding the edges of the abdominal wall in apposition during healing. In another embodiment, the components may be reversed such that the base or platform may be inserted from the exterior with prongs through the wall. Suture is then passed from one prong through the wall and up a second prong on same side of incision. Other spanning embodiments would apply here as well. In yet another embodiment, the anchor may comprise a base or platform with prongs. The prongs have one or more barbs along their length. The base or platform is inserted from the exterior abdominal wall with the prongs extending into but not through the abdominal wall. The barb(s) serve to retain the anchor in the abdominal wall. Provisions can be made on the base or platform (such as holes) for the attachment of suture(s). Suture can then be passed through the hole(s) and connect the anchor to another complimentary anchor on the opposite side of the incision to hold edges of the abdominal wall in apposition during healing.

Figure 12:
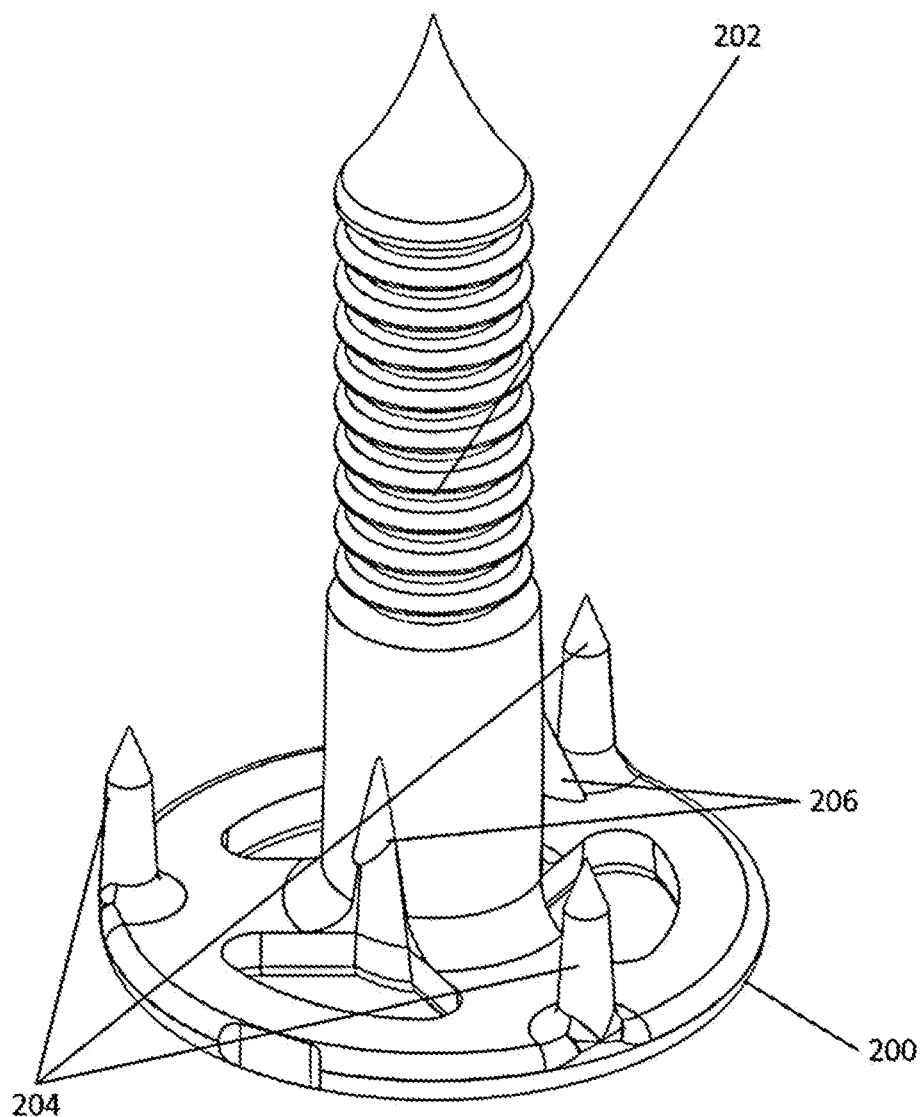
FIG. 12 shows a perspective view of an anchor with, e.g., one prong, with one or more barbs near a base of the prong and one or more tines.

In another embodiment (as shown in the perspective view of FIG. 12), the base may be circularly shaped (or any number of other shapes such as elliptical, ovular, etc.) with a single prong 202 extending normally or at an angle from the base. The prong 202 may similarly extend at a distance of, e.g., 1 to 25 mm (although longer lengths may be needed for unusually thick abdominal walls), from the base with a diameter of, e.g., 1 to 6 mm. The prong 202 may also be circularly shaped (or any other cross-sectional shapes as described herein) and while shown to extend from a center of the base, the prong 202 may be positioned at other locations over the base. Furthermore, the terminal end of prong 202 may be defined with a piercing tip, preferable of atraumatic shape, to facilitate the insertion of the prong 202 through the tissue during engagement (the piercing tip may be removed after tissue securement, as described herein) and a distal portion of the prong 202 may be configured to present a threaded, notched, or otherwise non-smooth outer surface for facilitating engagement and securement with a corresponding member, as further described herein.

Aside from the prong 202, the anchor 200 may further include one or more tines 204 that may also extend from the base at a distance of, e.g., 1 to 8 mm, with a diameter of, e.g., 1 to 6 mm. Tines 204 may extend at arbitrary or uniform locations from the base, e.g., from a circumferential position, and while three tines 204 are shown, fewer or greater number of tines 204 may be used to further secure the anchor to the tissue. Optionally, the prong 202 or tines 204 may have a notch, barb, or undercut 206 defined along the outer surface that may help secure the anchor to the tissue, making dislodgement less likely.

To protect the viscera, the anchors are typically installed with the prongs passed from the inside of the abdomen towards the outside. This safety measure does not restrict the anchors to only that usage and an alternative is to pass the prong from the outside of the abdomen towards the inside.

Figure 13:
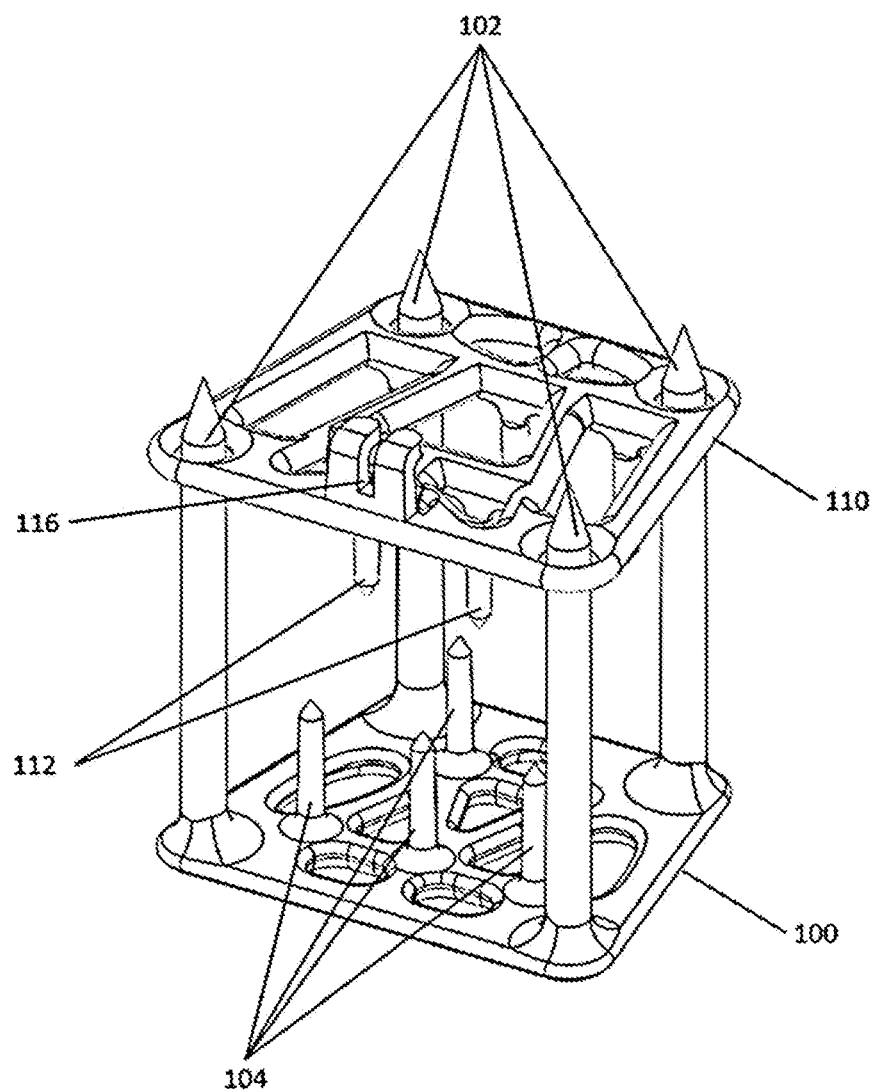
FIG. 13 shows a perspective view of an anchor with a first and second member with one or more prongs and one or more tines.

Anchors similar to the previous embodiments are ideally coupled to a second member 110, 410 having a base or platform (as shown in the perspective views of FIG. 13 and FIG. 14), preferable superficial to the anterior rectus sheath (fascia). In such embodiments the anchor 100, 400 may comprise a base (first member) with one or more prongs 102, 402 that are placed from the interior of the abdominal wall to its external surface, with the prongs 102, 402 extending through the thickness of the wall and a base or platform (second member) 110, 410 on the exterior of the wall which clips, snaps, or is otherwise attached to the prongs from the first member. The variation shown in FIG. 13 illustrates how the second member may also comprise a base defining one or more openings and one or more tines 112, 412 which extend from the base of the second member in the same manner as tines 104, 404. The second member may further define openings or receiving channels which correspond to the positioning of the prongs 102, 402 extending from the first member. In this manner, the second member may be positioned so that the prongs 102, 402 from the first member extend through the corresponding openings defined in the second member while allowing for the first member and the second member to maintain a parallel orientation relative to one another while sandwiching the tissue thickness between each of the members. The one or more tines 112, 412 of the second member may be oriented to point towards the first member, as shown, to further secure the tissue thickness between each of the members.

A stop or shoulder 116 may also be positioned to extend from the surface of the second member such that the shoulder 116 extends away in the opposite direction from the tines 112. The shoulder 116 may be positioned along or in proximity to an edge of the second member between the openings such that the shoulder 116 is positioned along the edge closest to a second opposing anchoring member for attachment of suture(s) or other spanning component such as a ball chain. Said sutures or chains can then be attached to similar provisions on a second anchor on the opposite side of the incision to hold edges of the abdominal wall in apposition during healing. Optionally shorter tines 104, 112 may be arranged on the first and/or second members that are designed to only extend through a portion of the abdominal wall, in addition to the prong(s). The tines 104 on the first member may penetrate the posterior rectus sheath where it is present. The tines 112 on the second member may penetrate the anterior rectus sheath. Any such tines 104, 112 may have a notch, barb, or undercut to make dislodgement less likely.

Figure 14:
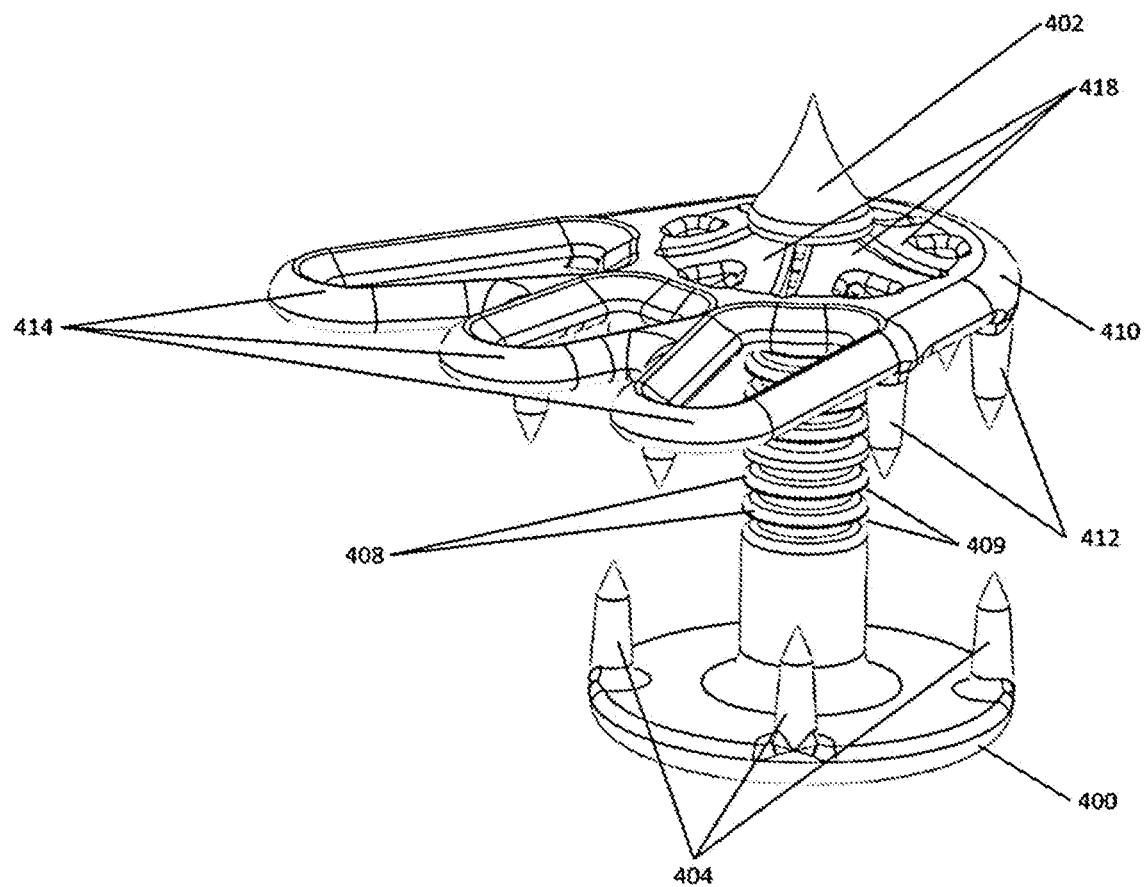
FIG. 14 shows a perspective view of an anchor with first and second members with, e.g., a single prong, and one or more tines.

FIG. 14 shows a second member 410 which may also engage with the prong 402 from the first member but this second member may define an opening sized for receiving the prong 402 through a central opening. The second member may further have one or more securement members 414 which extend from the second member to define one or more openings for engaging via a connector such as a suture with a second anchoring device when approximating tissue. The securement members 414 may extend planarly or angled to form any number of openings, e.g., one, two, three, or more openings, and the one or more tines 412 may extend transversely relative to the openings for engaging with the tissue.

Various tools may be used to measure force applied to the sandwiched tissue between the first and second member in order to limit pressure to a desired level (e.g., <32 mm Hg), thus preventing tissue necrosis or compromise.

Figure 15:
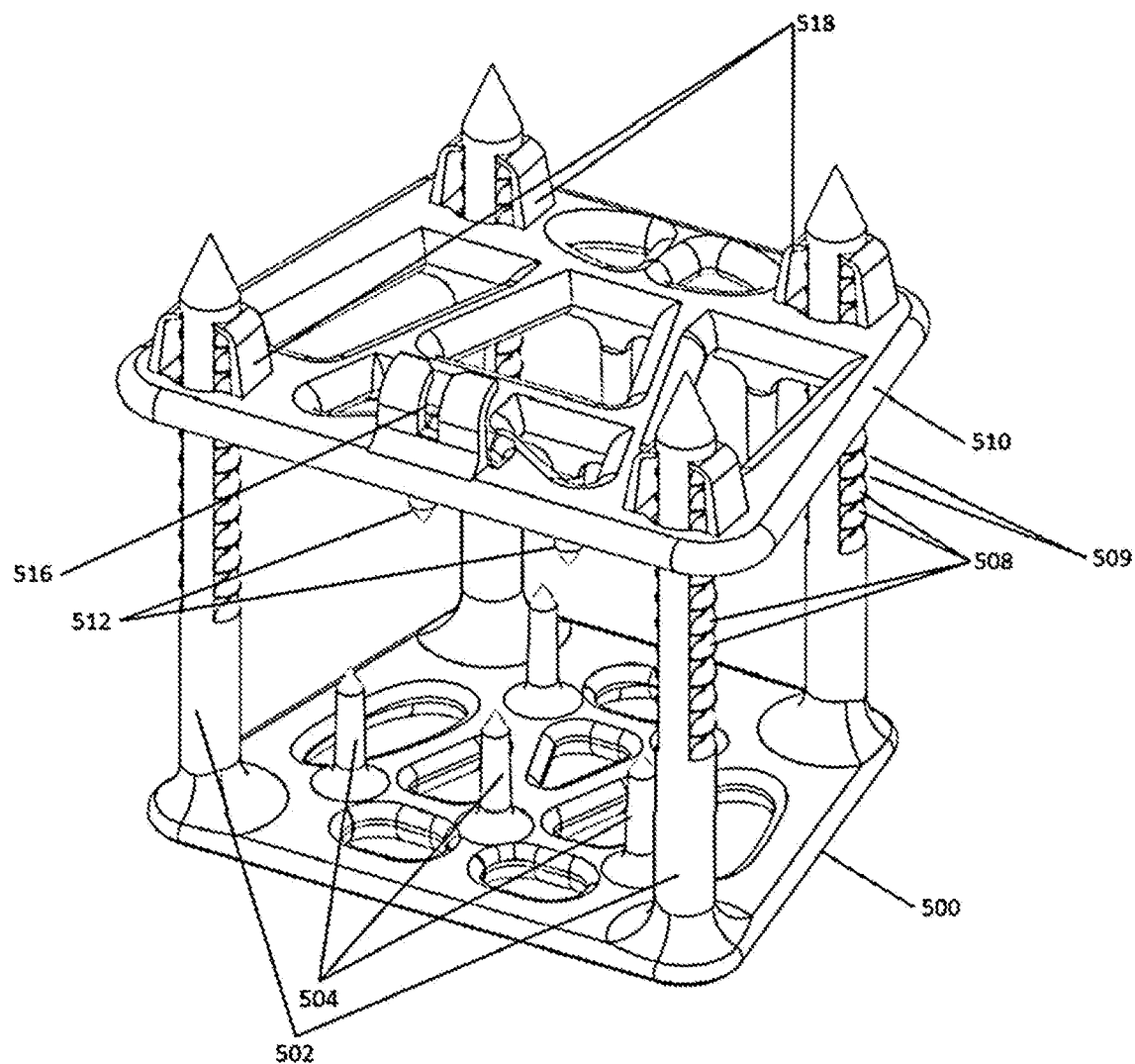
FIG. 15 shows a perspective view of an anchor with a first member and a second member which engages with the first member via, e.g., ratchet elements.

In one embodiment (FIG. 15), the anchor comprises a first member 500 (also referred to as an posterior plate or base), with one or more prongs 502 extending perpendicularly from the plate, as previously described, that are placed from the interior of the abdominal wall to the external surface with the prongs 502 extending through the thickness of the abdominal wall and a second member 510 (also referred to as an anterior plate or base), on the exterior of the abdominal wall. The second member 510 has integrated features such as flexible fingers 518 that engage with notches 508, 509 or similar geometry on the prongs 502 from the plate. The flexible fingers 518 may be configured as cantilevered members which are biased into contact against the prong surface to allow the second member 510 to slide down the prongs 502 towards the first member but resist sliding off of the prongs (away from the plate) due to the engagement of the fingers 518 against the notches 508, 509 when urged in the opposite direction. Alternatively, the flexible fingers 518 on the second member 510 may be replaced by an additional piece or pieces such as pawls which allow for similar movement down the prongs 502 and resist movement up the prongs 502. The fingers 518 or pawls may be arranged on one or more sides of the prongs 202. In FIG. 15, flexible fingers 518 are shown which act on two sides of the prongs. Specifically, a posterior plate 500 has a prong or prongs 502 with ridges or rings provided on all or part of each prong 502. A second member 510 is provided which has a hole configured to slip over the prong 502.

In each of these embodiments described, the first member may alternatively be referred to as a posterior plate or base due to its relative positioning within the body and the second member may alternatively be referred to as an anterior plate or base also due to its relative positioning within the body and relative to its position with respect to the posterior plate or base.

Figure 16:
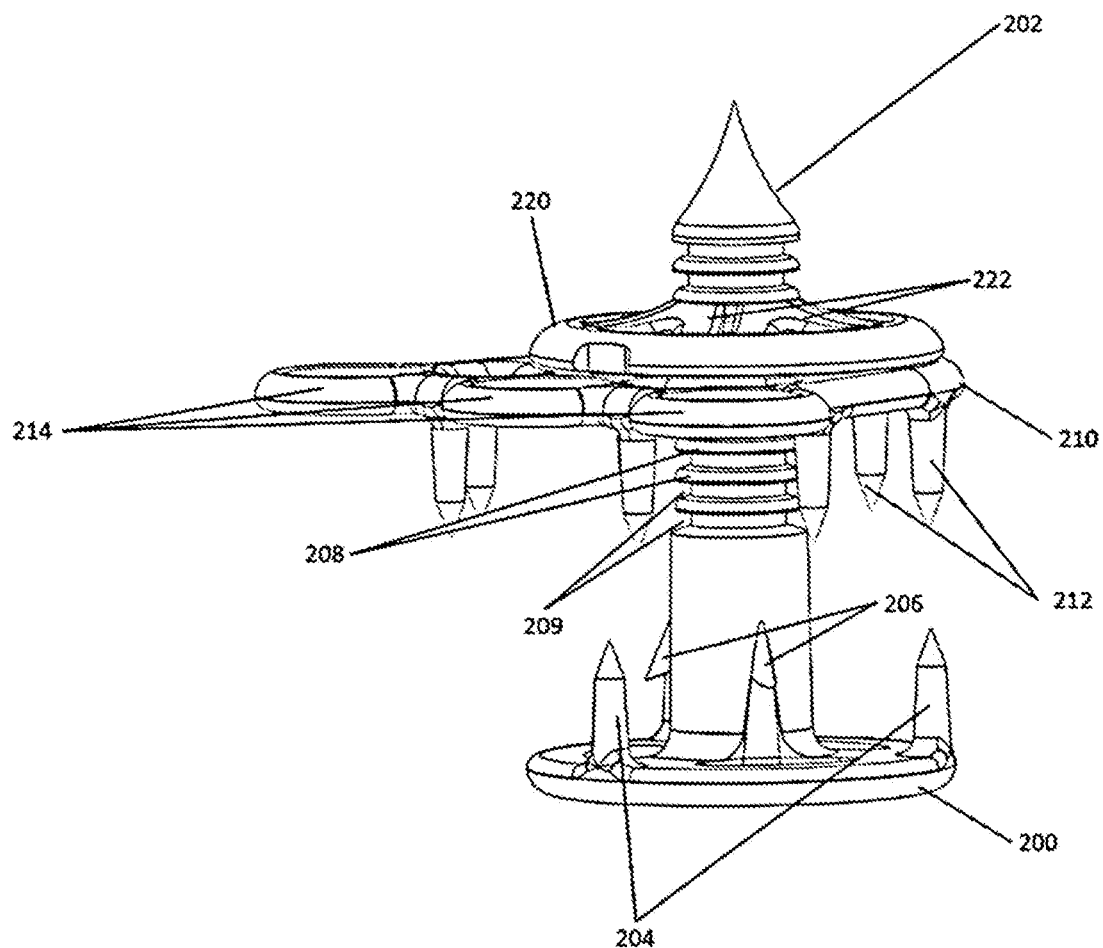
FIG. 16 shows a perspective view of an anchor with a first member, a second member, and a third member which restrains the movement of the second member relative to the first member.
Figure 17:
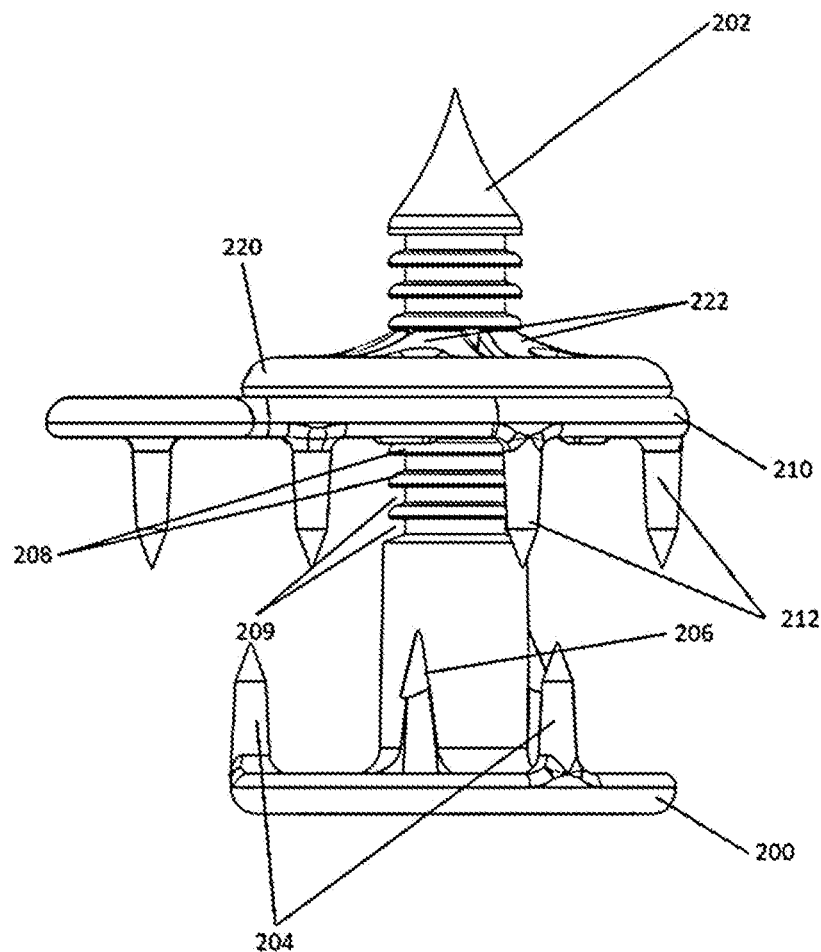
FIG. 17 shows a side view an anchor with a first member, a second member, and a third member which restrains the movement of the second member relative to the first member.

In another embodiment, as shown in FIGS. 16 and 17, the anchor may comprise a first member 200 with one or more prongs 202 that may be placed from the interior of the abdominal wall, and with the prong(s) extending through the thickness of the abdominal wall where a second member 210 may be engaged with the prong 202 such that the second member 210 is positioned upon the exterior of the abdominal wall. Whether the second member 210 is secured to the prong 202, the second member 210 may be further limited in its movement relative to the first member 200 by a third member 220, which may function as a retainer and can embody any number of configurations, e.g., clips, snaps, screws, or is otherwise attached to the prongs 202 from the first member. The third member 220, shown as a ratchet button in this example, may be configured to correspond in size or diameter to the first member 200 while further having one or more cantilevered fingers 222 configured to extend radially inward within the opening through which the prong 202 may be inserted to slip over the ridges on the outer surface of the prong 202. As the fingers 222 slip over the ridges, they may flex away from the second member 210. The third member 220 may be advanced down the prong 202 until it makes contact with the second member 210 (compression of the tissue between the first and second members may be allowed). Alternatively, the third member 220 and second member 210 may be preassembled prior to being advanced down the prong 202.

Figure 18:
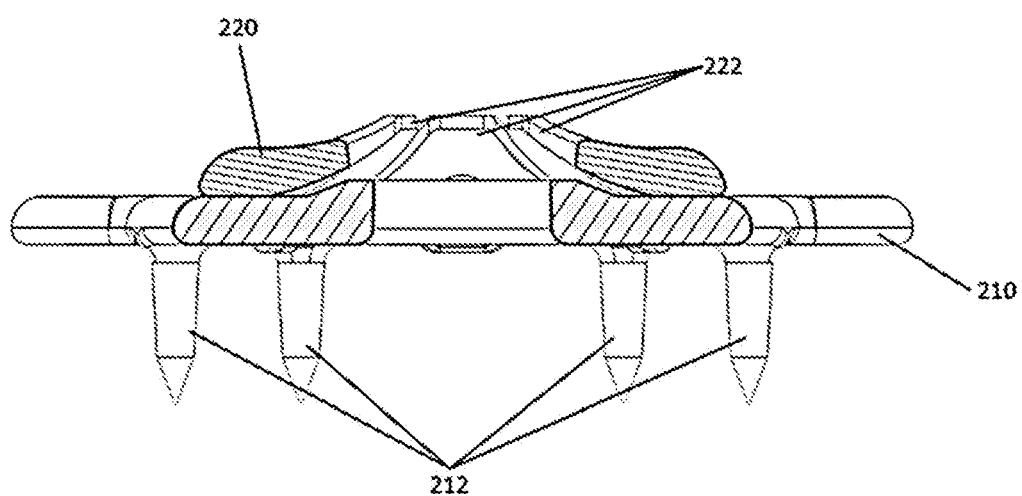
FIG. 18 shows a cross-sectional side view of the second and third members where the surfaces are configured to limit the ability of the fingers of the button to flex towards a posterior plate.

In some embodiments (as shown in the cross-sectional side view of FIG. 18), the geometry of the contact surfaces of the second member 210 and third member 220 are configured to prevent or limit the ability of the fingers 222 of the third member 220 to flex toward the second member 210. When pressure is applied to the second member 210 which would tend to separate the second member 210 from the first member 200, it pushes against the third member 220 which would tend to cause the fingers 222 to flex toward the first member 200 in order to expand to an effective diameter greater than the ridges on the prong 202. However, as the second member 210 is limiting the flex of the fingers 222 in that direction, the forces that the ratchet can withstand are much higher than an unsupported ratchet. The third member 220 and second member 210 can be pre-assembled or manufactured in such a way that the mating surfaces between the flex fingers 222 and the second member 210 still limit the ability of the flex fingers 222 to flex toward the first member 200 but the user can apply them as one piece to the first member 200.

Figure 19:
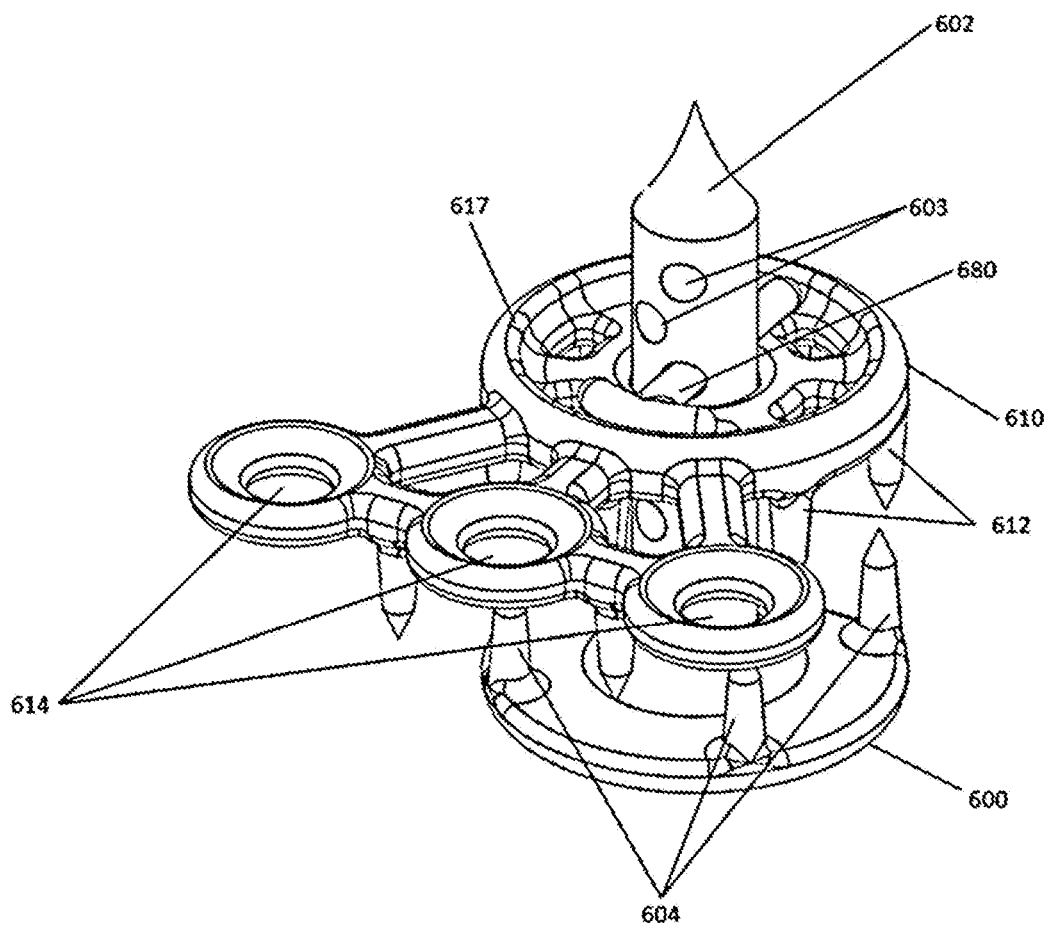
FIG. 19 shows a perspective view of an anchor with a first and second member with a third member configured as a removable pin which restricts the movement of the second plate relative to the first plate when the pin is engaged.
Figure 20:
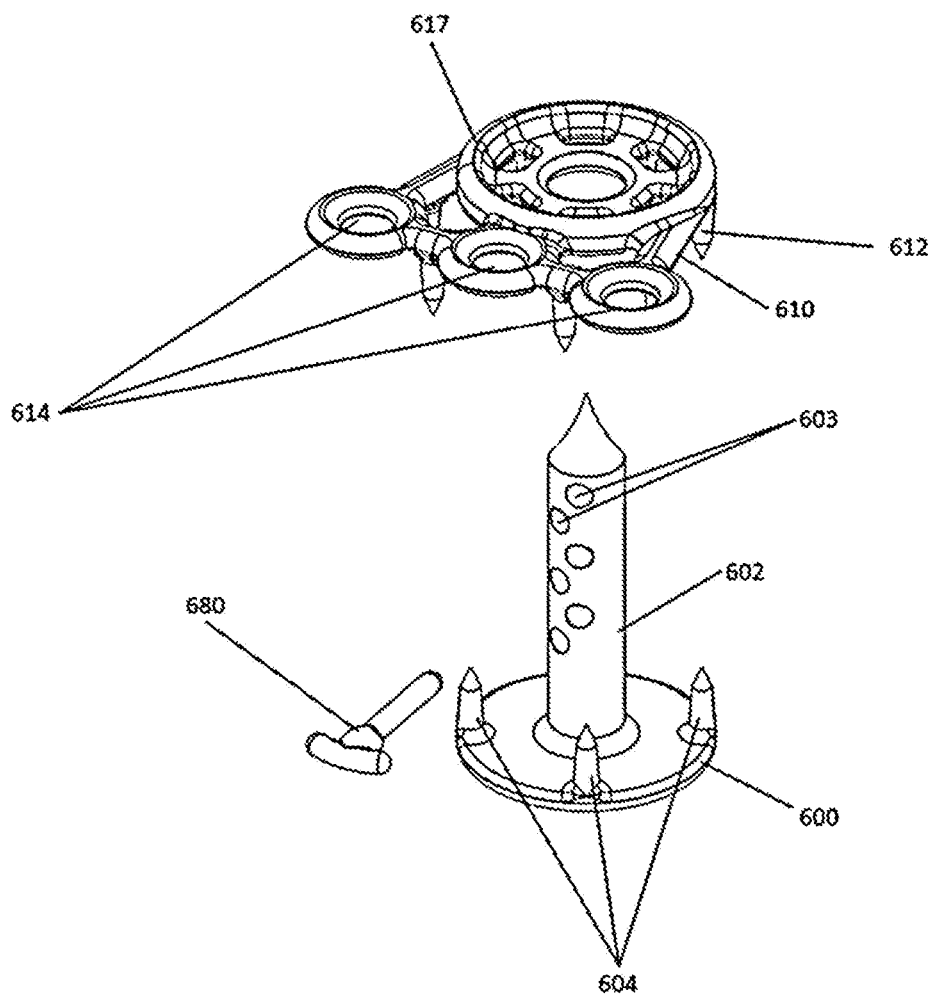
FIG. 20 shows an exploded perspective view of an anchor with a first and second member with a third member configured as a removable pin.
Figure 21:
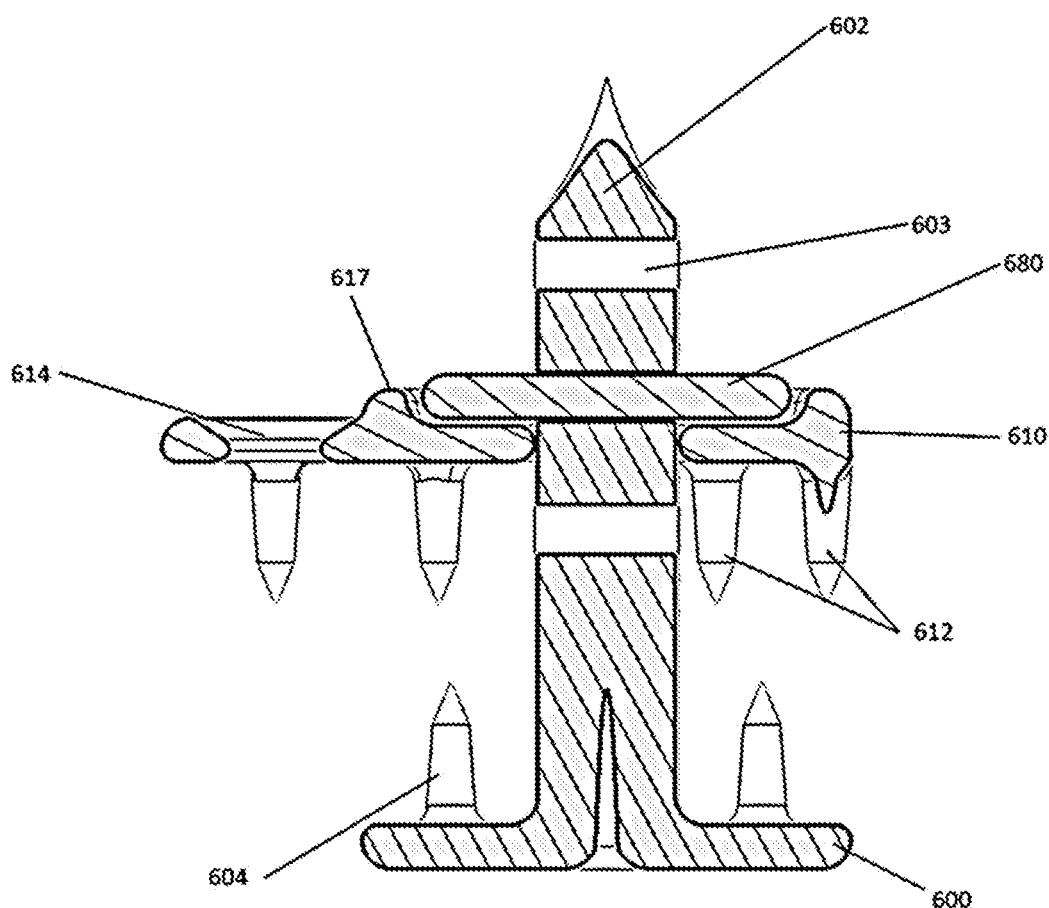
FIG. 21 shows a cross-sectional side view of an anchor with a first and second member with a third member configured as a removable pin which restricts the movement of the second plate relative to the first plate when the pin is engaged. In turn, the second plate restricts the movement of the third member from releasing from the first member.

In yet another embodiment (as shown in the perspective view of FIG. 19 as well as FIGS. 20 and 21) the first member 600 has a prong or prongs 602 with one or more holes, openings, or channels 603 defined through the prong 602 orthogonally to the primary axis of the prong 602. A second member 610 is provided which has a hole configured to slip over the prong 602. The third piece may be comprised of one or more pins 680 which are removable and of a size which enables it to be inserted into the channels 603 defined through the prong 602. The pins 680 may be simple cylinders or may have additional features such as a spring connecting two or more pins 680 (for insertion into holes on more than one prong at a time), a head or other feature for improved handling, or a 'T' shape which simultaneously allows for better handling and prevents the pin 680 from passing completely through the prong 602. An additional improvement on this design may comprise a ridge 617 or other feature to the second member 610 which may extend circumferentially. By over-compressing the second member 610, tissue, first member 600 "sandwich", the pin 680 can be inserted into a channel 603 on the prong 602 and when the sandwich is released, the ridge 617 on the second member 610 may prevent the ability of the pin 680 from sliding out of the opening, functioning as a stop for the pin 680 release.

Another embodiment may comprise a ring that enters the channel 603 from one or both sides.

Figure 22:
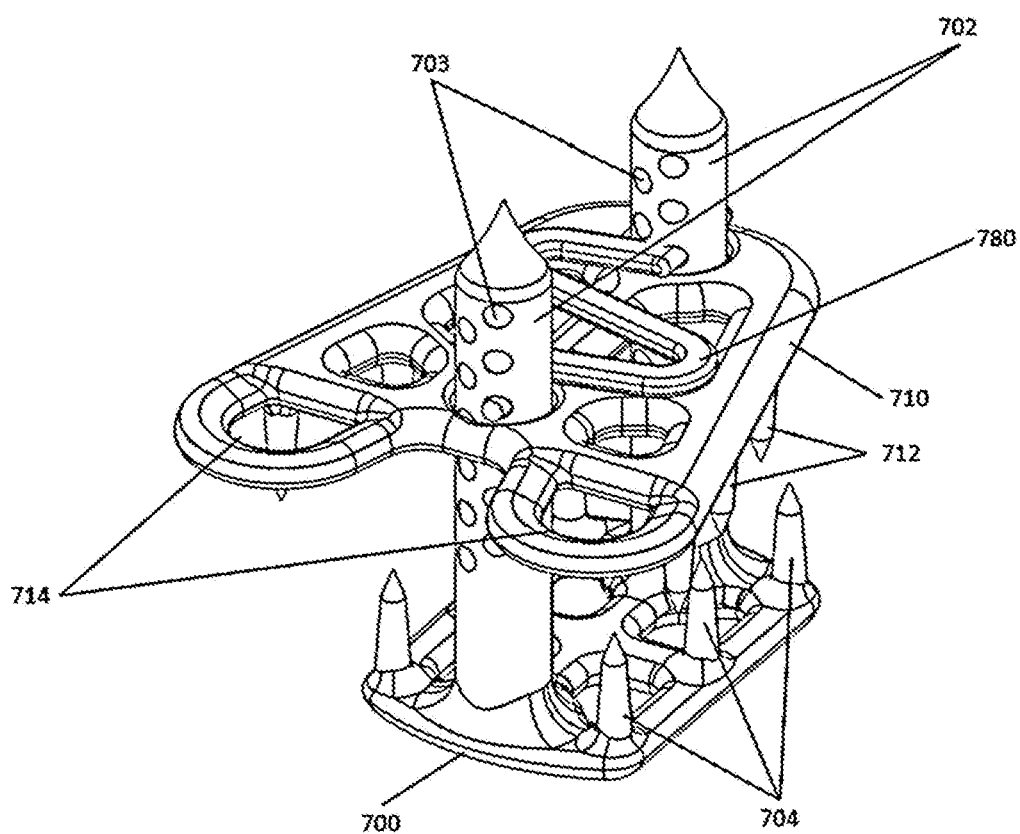
FIG. 22 shows a perspective view of an anchor with a first and second member with a third member configured as two pin segments connected by a flexible element where the third member restricts the movement of the second plate relative to the first plate when the pins are engaged.
Figure 23:
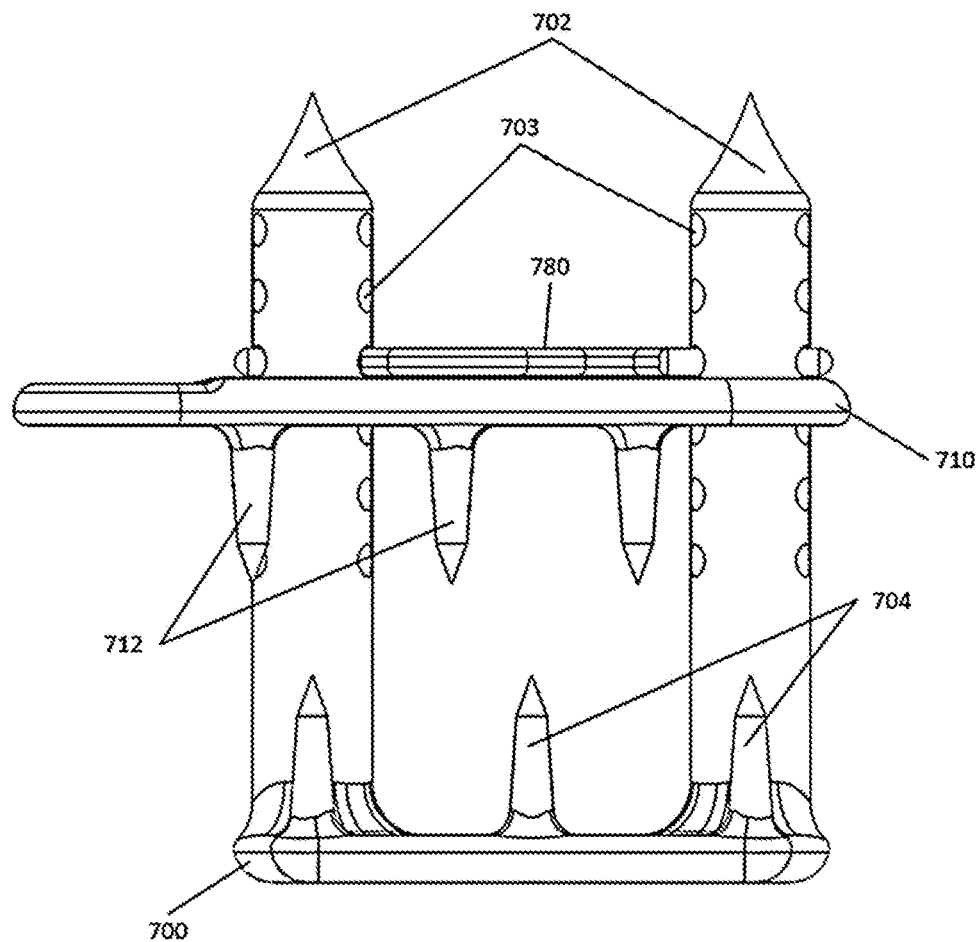
FIG. 23 shows a side view of an anchor with a first and second member with a third member configured as two pin segments connected by a flexible element where the third member restricts the movement of the second plate relative to the first plate when the pins are engaged.
Figure 24:
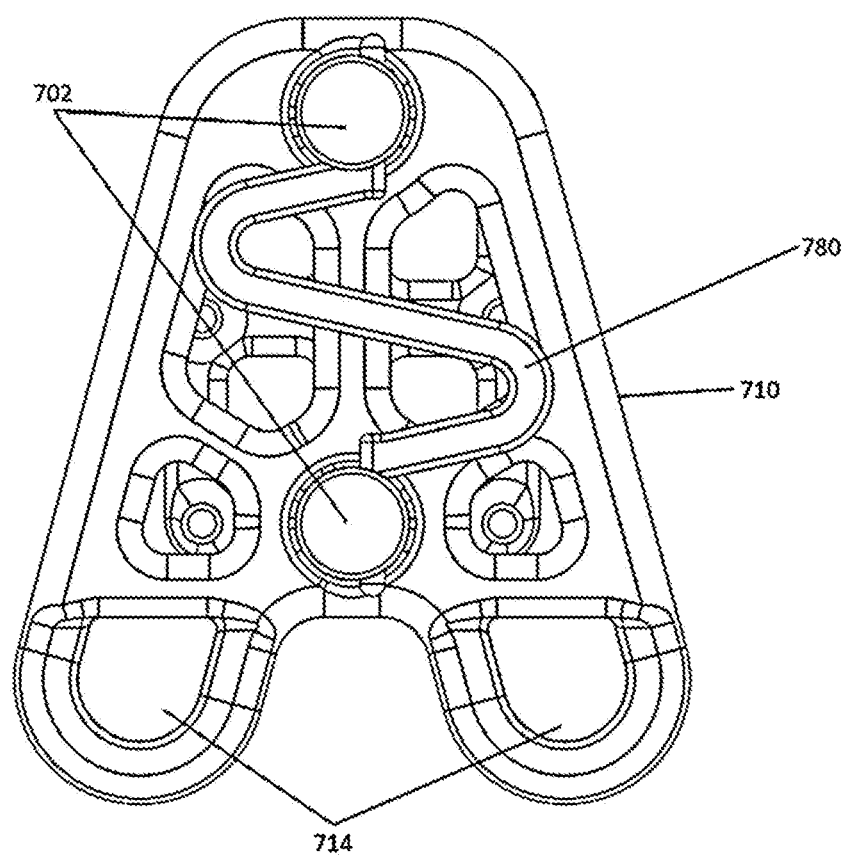
FIG. 24 shows a top view of an anchor with a first and second member with a third member configured as two pin segments connected by a flexible element where the third member restricts the movement of the second plate relative to the first plate when the pins are engaged.
Figure 25:
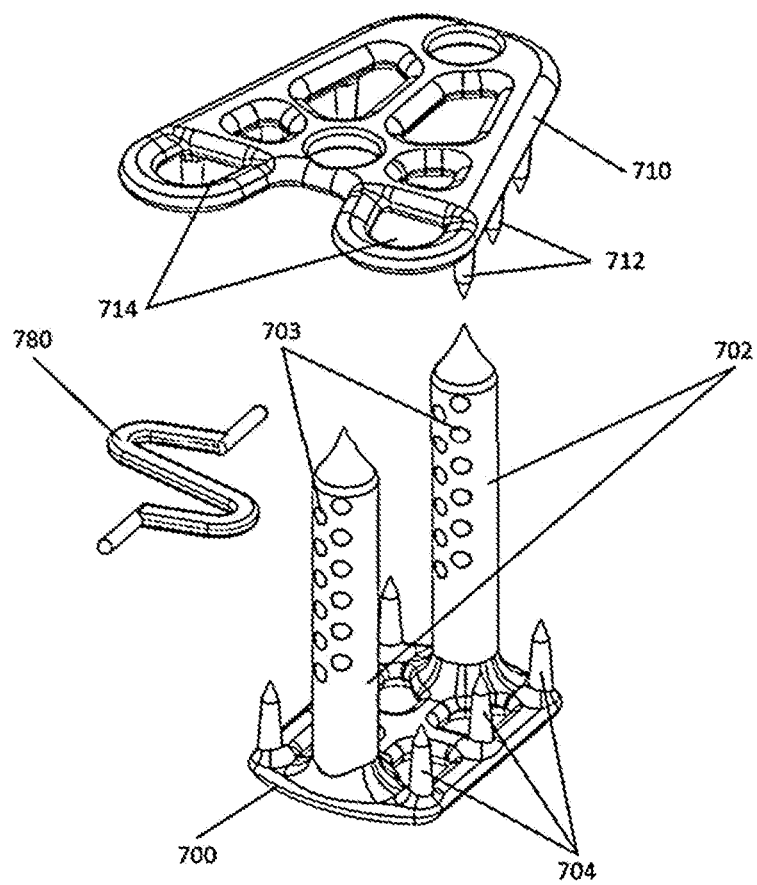
FIG. 25 shows an exploded perspective view of an anchor with a first and second member with a third member configured as two pin segments connected by a flexible element.
Figure 26:
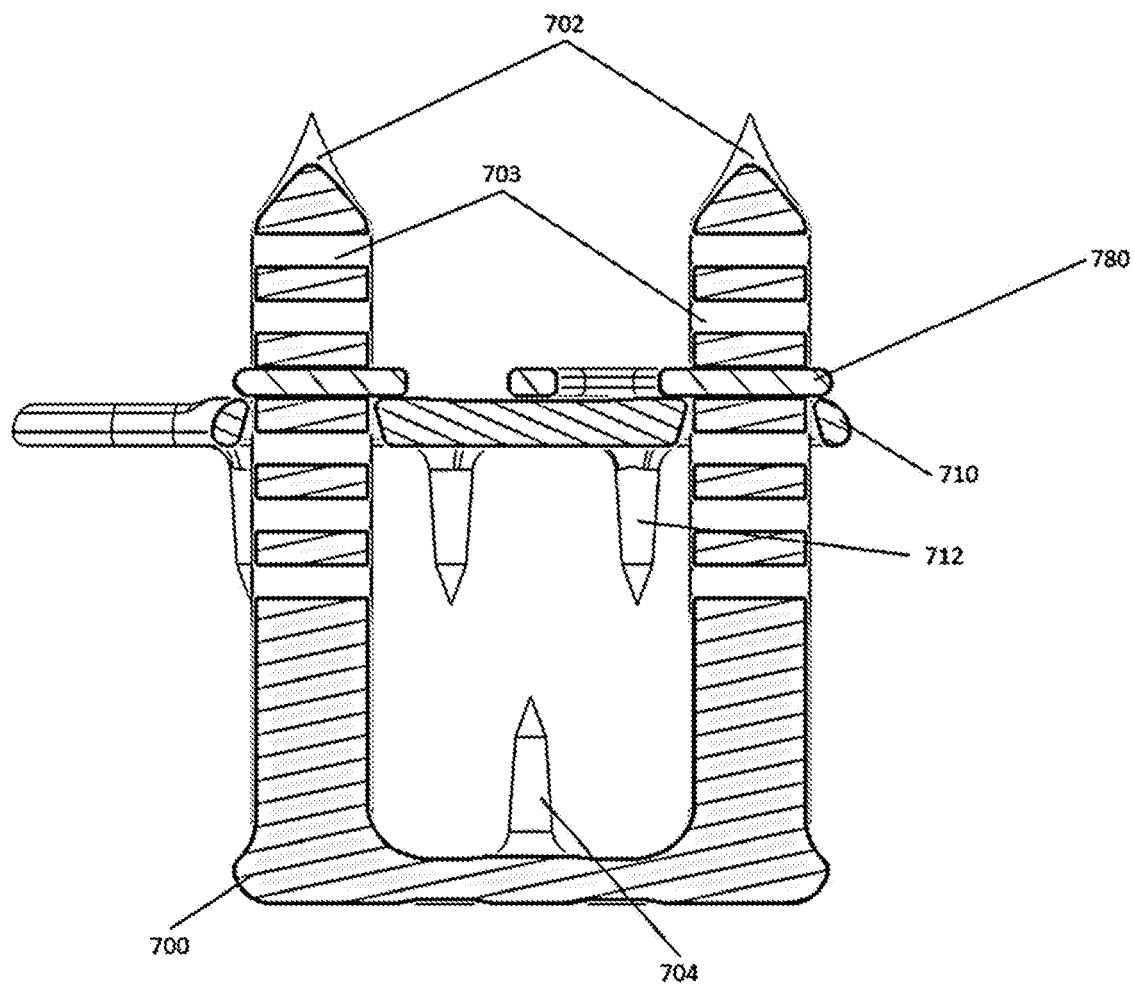
FIG. 26 shows a cross-sectional side view of an anchor with a first and second member with a third member configured as two pin segments connected by a flexible element where the third member restricts the movement of the second plate relative to the first plate when the pins are engaged.

In yet another embodiment (as shown in the perspective view of FIG. 22 as well as FIGS. 23 to 26), the first member 700 has a plurality of prongs 702 with one or more holes, openings, or channels 703 defined through the prongs 702 orthogonally to the primary axis of the prong 702. Although two prongs 702 are shown in this variation, other embodiments may incorporate more than two prongs 702. In any case, the prongs 702 may be positioned to extend parallel to one another in order to facilitate their engagement with a second member 710. Moreover, the prongs 702 are shown to extend orthogonally relative to the first member 700; however, the prongs 702 may each extend in parallel at an angle relative to the first member 700, if so desired. The second member 710 is provided having a number of holes configured to slip over the prongs 702 in a corresponding manner. The third piece 780 may be comprised of one or more pins which are connected at their proximal ends to one another via a connecting member which may define a curved or arcuate configuration. In this manner, the curved connecting member may be coupled to a respective pin at each terminal end. The pins are removable and of a size which enables it to be inserted into the channels 703 defined through the prong 702. In this manner, the pins may be inserted into their respective openings along each respective prong 702 such that the curved connecting member provides a biasing force, much like a spring, which urges each pin to remain in its respective opening and to prevent accidental release of the pins from the prongs 702. To release the pins for adjusting the second member 710, the pins may be urged towards one another against the biasing force provided by the curved connecting member and to re-engage the pins into the holes, the pins may be simply released such that the connecting member urges them away from one another for engagement within the respective holes. The pins 780 may be simple cylinders or may have additional features such as a spring connecting two or more pins 780 (for insertion into holes on more than one prong at a time), a head or other feature for improved handling, or a 'T' shape which simultaneously allows for better handling and prevents the pin 780 from passing completely through the prong 702.

Figure 27:
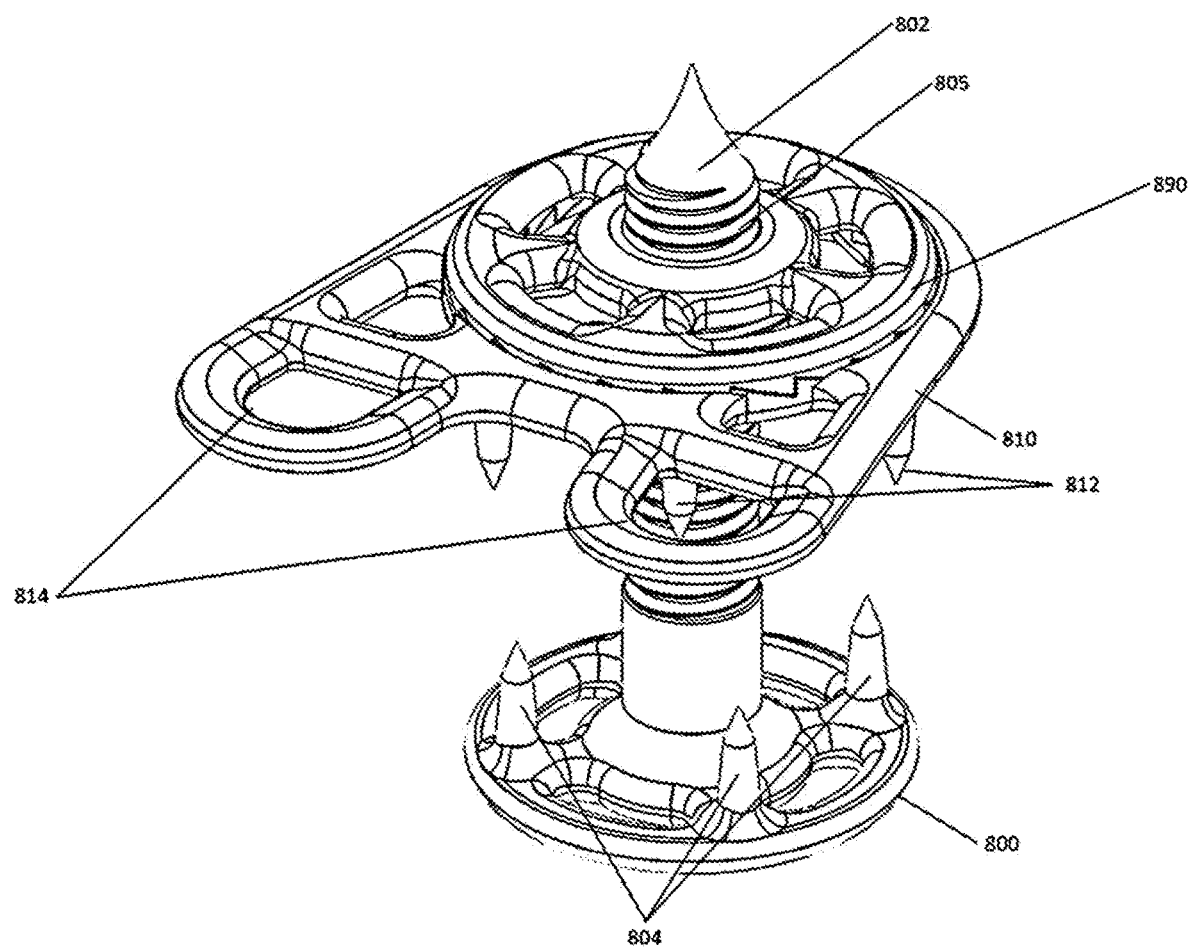
FIG. 27 shows a perspective view of an anchor with three members with the third member configured as a nut which may be engaged onto threads of a prong.
Figure 28:
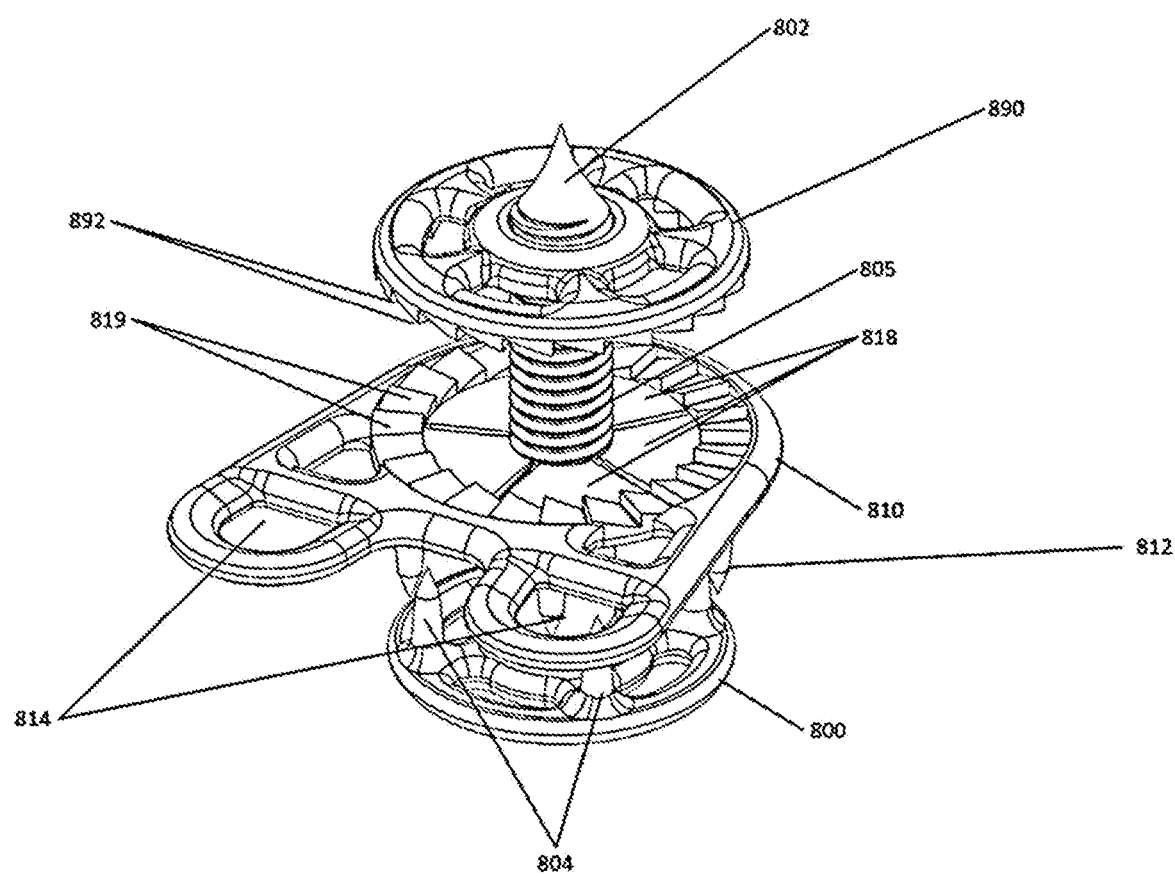
FIG. 28 shows a perspective view of an anchor with three members wherein the third member is configured as a nut which may be engaged onto threads of a prong and where the second member has ratchet elements which also engage the third member in position on the prong.

In another embodiment as shown in FIGS. 27 and 28, a threaded second member 810 can be screwed onto a threaded prong 805 from the first member 800. However, if the second member 810 is threaded onto the prong 805, it may not be feasible to have smaller, secondary tines on the second member 810 and/or the first member 800 due to the tines not being able to rotate in tissue. Therefore, the screw attachment mechanism may be comprised of a three-member design with a threaded third member 890 restricting the motion of the second member 810 relative to the first member 800.

In another embodiment, the third member 890 may be comprised of a nut which threads down the prong 802 from the first member 800. Preferably, to secure the third member on the prong, the mechanism utilizes a threaded feature 805 in conjunction with a ratchet to provide both a clamping force and a locking mechanism for the device when assembled. The first member 800 and second member 810 of the device are inserted into the abdominal wall similarly to previous designs. The threaded ratchet 890 mates with the posterior prong 802 forcing the threaded ratchet onto the second member 810. The second member 810 also has mating ratchet teeth 819 that interact with opposing geometry 892 on the threaded ratchet. Once a certain compression is achieved on the abdominal wall tissue between the first and second device plates, the ratchet will not disengage, thus resisting any tendency for the button to unscrew from the prong.

In an alternate embodiment (as shown in the perspective view of FIG. 28), the second member 810 has fingers 818 or other elements that act as a rachet on the prong threads 805, allowing the second member 810 to be placed (axially) onto the prong and held in position while the third member 890 is screwed onto the prong 802.

Figure 29:
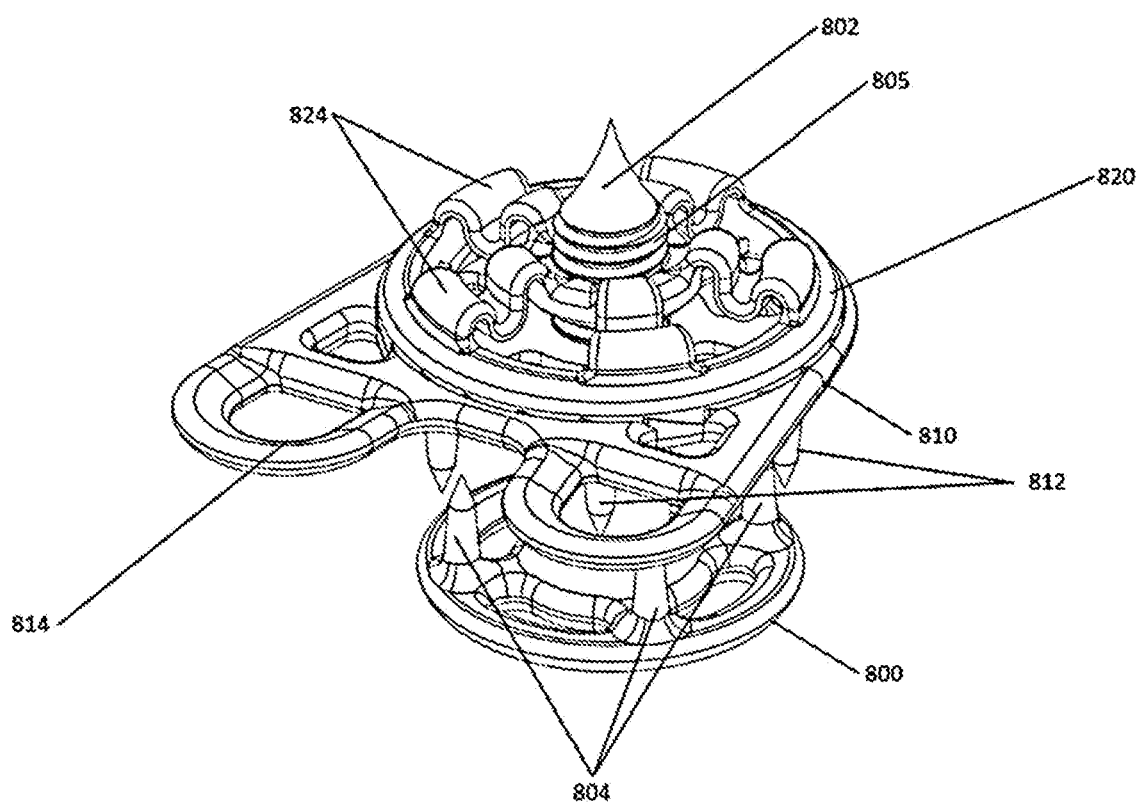
FIG. 29 shows a perspective view of an anchor with three members with the third member being a nut which is screwed onto threads of the prong and where the third member has flexible spring members.
Figure 30:
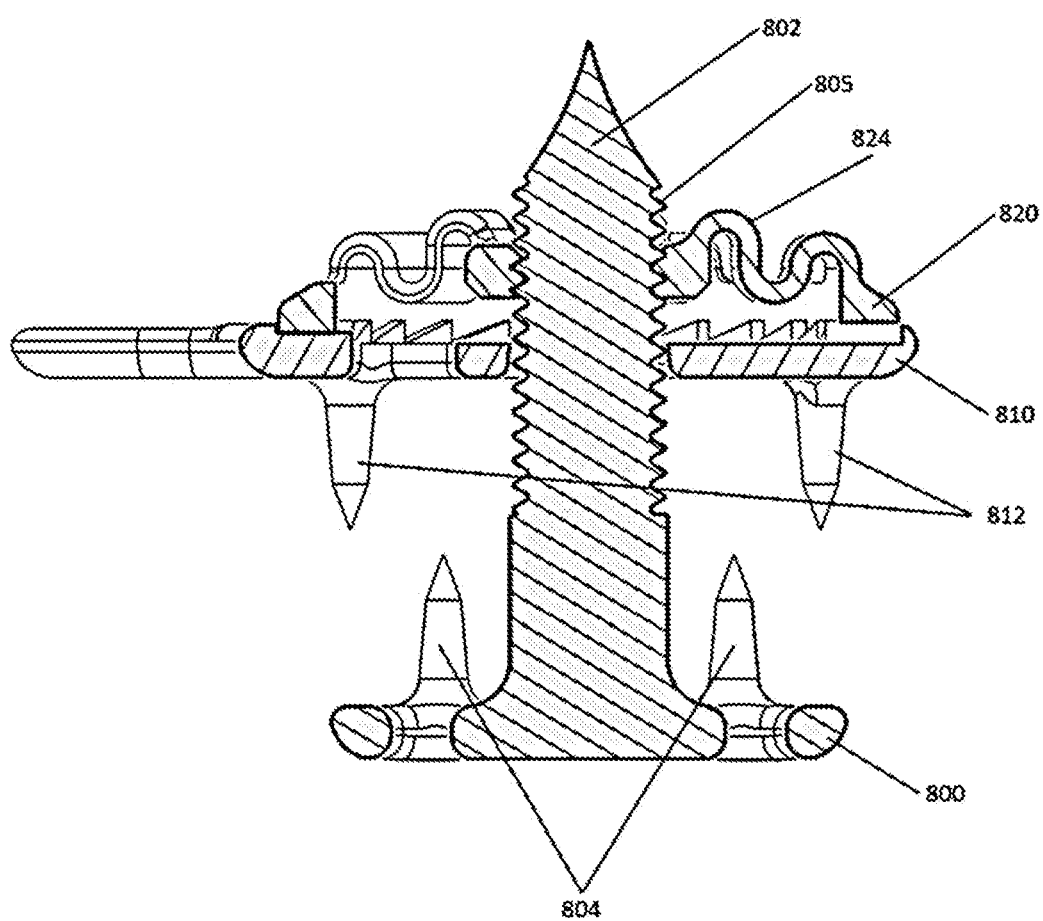
FIG. 30 shows a cross-sectional side view of an anchor with three members with the third member being a nut which is screwed onto threads of the prong and where the third member has flexible spring members.

In yet another embodiment (as shown in the perspective view of FIG. 29 and cross-sectional view of FIG. 30), the third member 820 may incorporate flexible elements 824 integrated into its structure. These flexible elements 824 may extend radially inward between selected locations about the circumference of the member 820 and connecting to a central ring member which may be coupled to the prong 802. The flexible elements 824 may define one or more curved members which allow for the central ring member to flex via the flexible elements 824 relative to the outer ring member forming the circumference of the third member 820 so that the flexible elements 824 act as a pressure relief spring allowing the second member to float as needed under higher pressures after implanting the device. Such a capability is relevant if expansion of the abdominal wall from muscle contraction or edema causes higher compression forces between the device plates.

Figure 31:
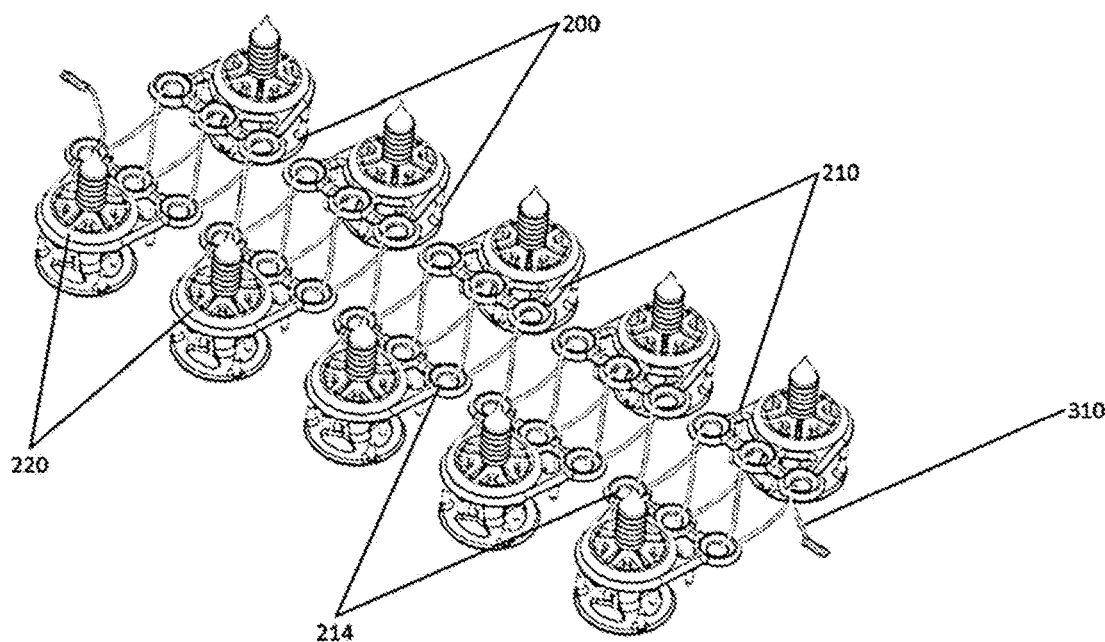
FIG. 31 shows several anchors positioned opposite to one another in adjacent pairs with suture interconnecting each of the anchors through holes in the devices for approximating two opposed tissue edges towards one another.

In embodiments where any of the anchors described above and the suture are bioabsorbable, each of these components may bioabsorb into the patient's body, thus leaving no permanent footprint of foreign material that can later lead to complications such as infection. One or more holes 214 may be placed in the device to allow for suture 310 passage, as shown in the assembly perspective view of FIG. 31. The suture 310 from one anchor can connect to an anchor on the contralateral side in a running pattern so that each of the anchors are interconnected to one another. In other examples, pairs of anchors may be attached to one another via sutures in an interrupted pattern. The suture and anchor complex may hold the abdominal wall edges in apposition while healing occurs. The holes may be provided on the anterior, posterior, button (if present), or multiple members of the anchor.

Figure 32:
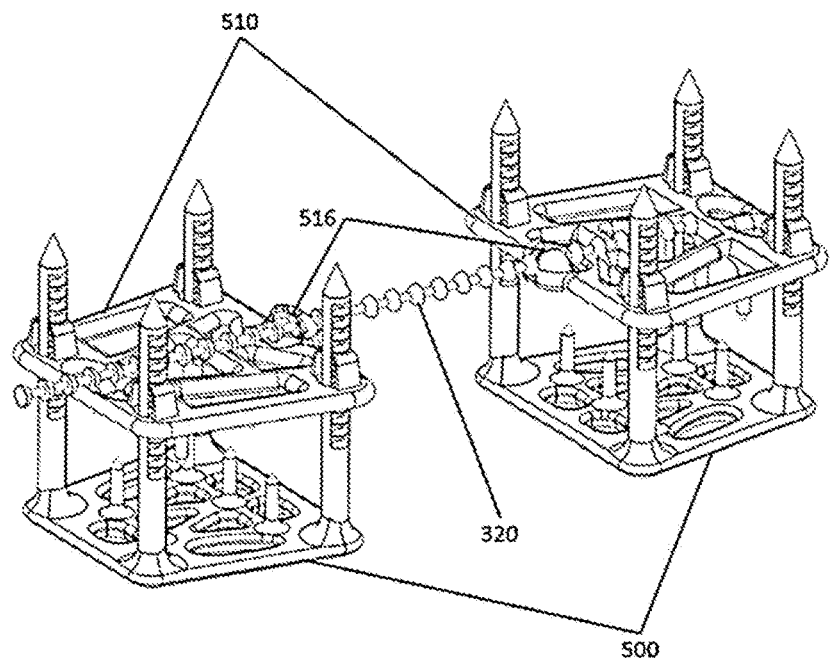
FIG. 32 shows a perspective view of a pair of devices connected by a flexible member having a plurality of preset stops such as a ball chain.
Figure 33:
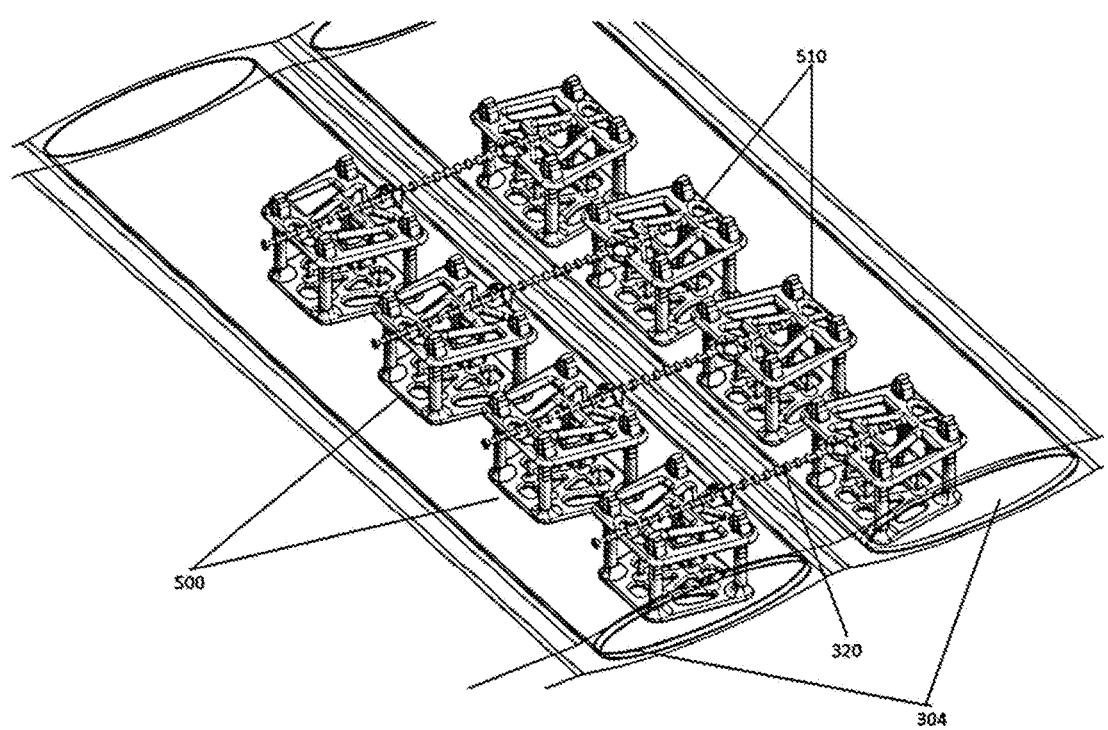
FIG. 33 shows a perspective view of a multiple pairs of devices as in FIG. 32 implanted into the abdominal wall.
Figure 34:
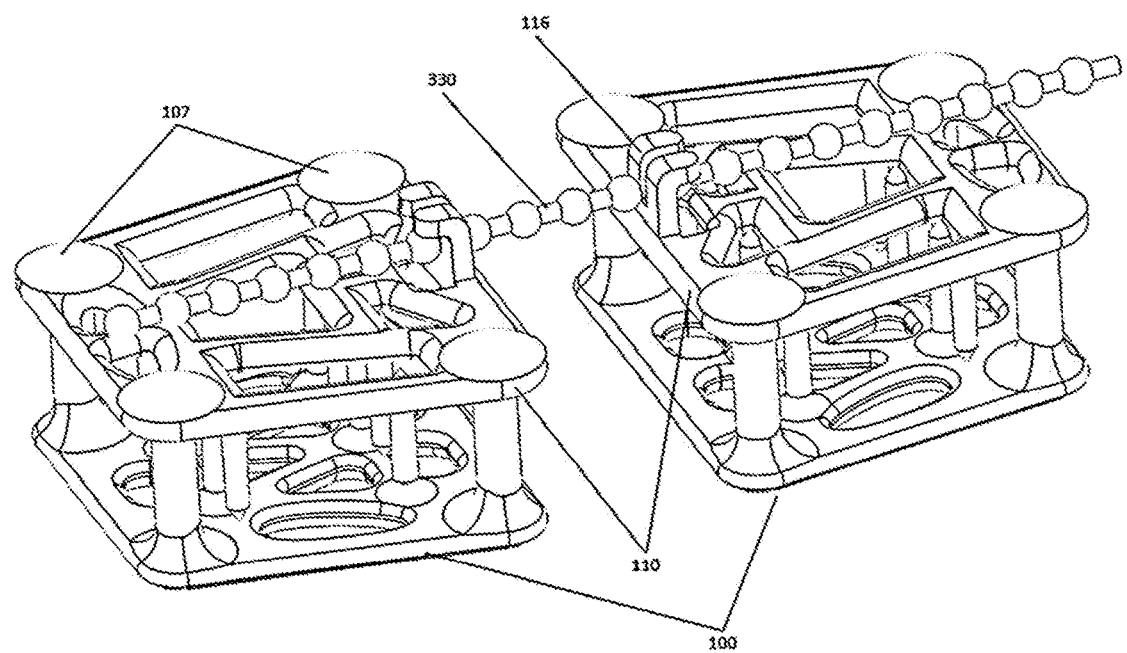
FIG. 34 shows a perspective view of another embodiment of a pair of devices connected by a flexible member having a plurality of preset stops such as a ball chain.

In yet another embodiment, the anchor may incorporate a stop or shoulder 516, 116, as shown and described herein, for attachment of a ball (or bead) chain 320, 330 or similar structure (as shown in the perspective views of FIGS. 32, 33, and 34). The ball chain 320, 330 can also take the form of a strap with notches that engage with a finger or cam on the anchor to resist movement of the strap or ball chain 320, 330 relative to the anchor. The anchor may comprise various methods of holding a suture or ball chain 320, 330 (in lieu of a suture) under tension between two devices, one on each side of the closure. In other embodiments, the spanning sutures or ball chain 320, 330 might be replaced by spanning screw(s), staple(s) (adjustable or fixed), or other structure that crosses from an anchor to a complimentary anchor on the other side of the incision in order to cause and hold apposition of the abdominal wall tissues.

In many embodiments described, the prong(s) extending from the first member may be cut, broken, or melted above the second (or third) member after assembly to limit excessive length of prongs protruding above the second and/or third member into or through subcutaneous tissues superficial to the abdominal wall. The ball (or bead) chain or strap (if used in lieu of a suture) may also be cut, broken, or melted to remove excess length beyond the attachment points on the base or platform.

Figure 35:
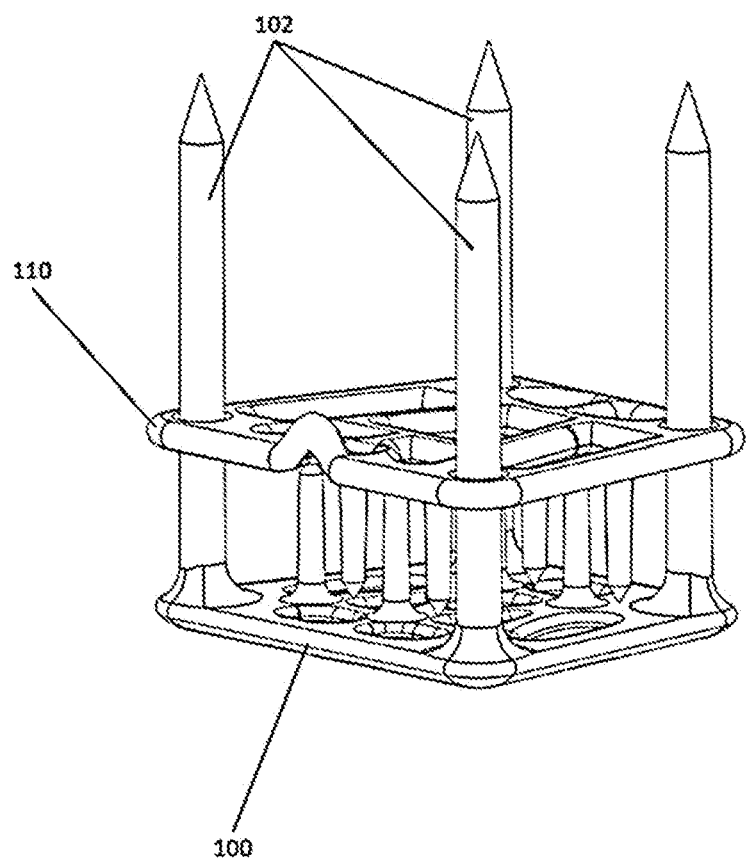
FIG. 35 shows a perspective view of a device having one or more prongs from a first member inserted through corresponding openings in the second member.
Figure 36:
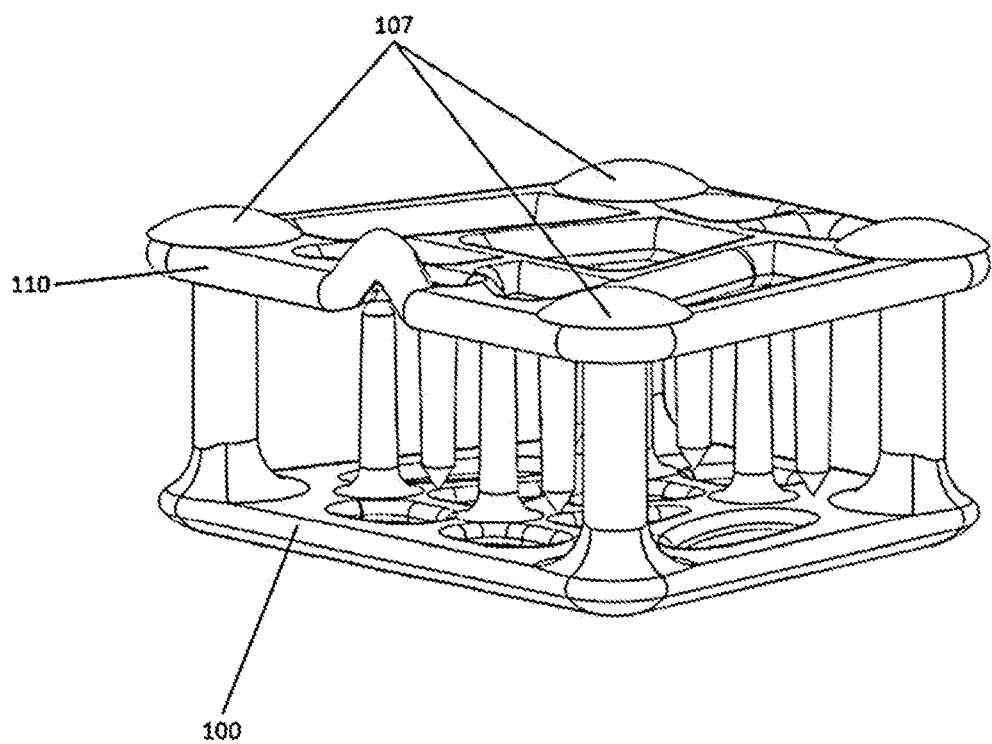
FIG. 36 shows a perspective view of a device with the prongs shortened and reconfigured or deformed such as through melting to retain the second member.

In another embodiment, the anchor comprises a first member with prong(s) that are placed from the interior of the abdominal wall to the external surface, as described herein and as shown in the perspective view of FIG. 35, with the prong(s) 102 extending through the thickness of the wall and a second member on the exterior of the wall which is assembled to the first member by slipping onto the prongs 102 from the first member. After assembly of the first member to the second member, energy is applied to the prong(s) 102 of the first member to deform them 107, preventing the second member from slipping off the prong (s) 102 of the first member (as shown in the perspective view of FIG. 36).

Figure 37:
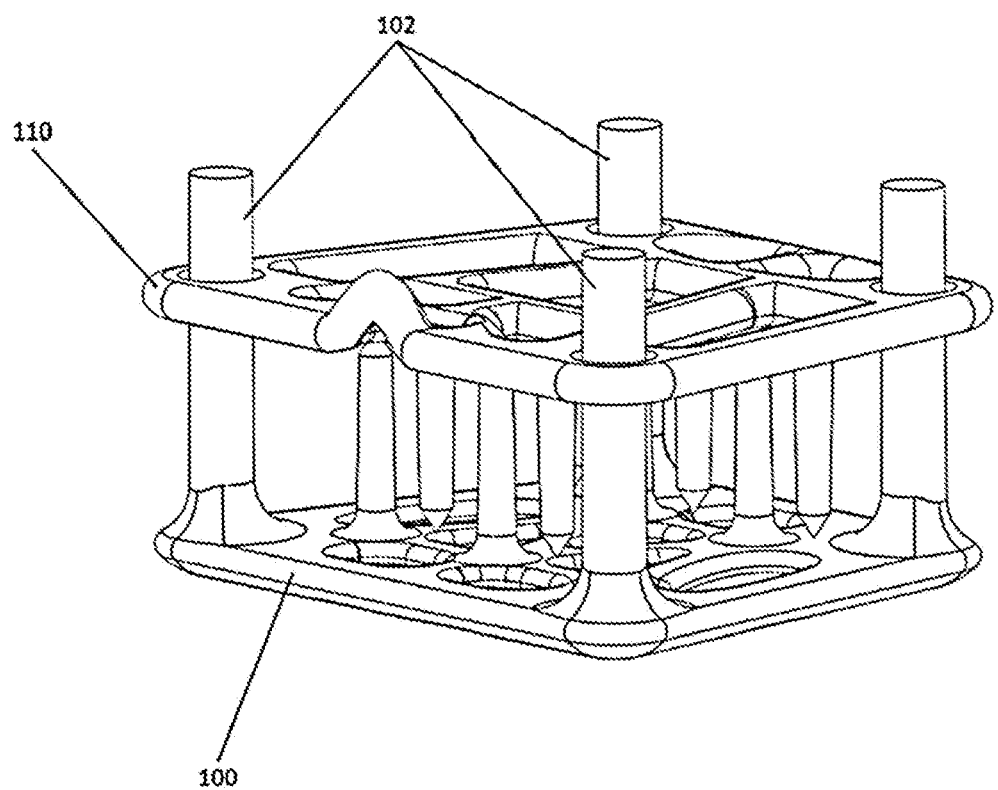
FIG. 37 shows the device from FIG. 35 with transected prongs.

Optionally, the prongs 102, 202, 402, 508, 602, 703, 802 of the first member may be cut or broken (as shown in the perspective view of FIG. 37) at a desired distance relative to the second member, before, or instead of the application of the energy to eliminate excess material. The energy may be applied to the prongs through direct thermal means (heat staking), ultrasonic (US) energy, infrared (IR) radiation, mechanical vibration or rotation (friction), or other methods amenable to intra-operative use. The energy is used to raise the temperature of the prong material above the glass transition temperature ($T_g$) or melt temperature ($T_m$). When the appropriate temperature is reached, pressure is applied to deform the prong creating a 'head' or similar deformation that mechanically prevents the second member from slipping up off the prongs of the first member. Alternatively, similar energy may be applied to material of both the first and second member to weld the two members together.

The applications of the devices and methods discussed below are not limited to wound closure but may include any number of further treatment applications. Moreover, such devices and methods may be applied to other treatment sites within the body. Modification of the above-described assemblies and methods for carrying out the invention, combinations between different variations as practicable, and variations of aspects of the invention that are obvious to those of skill in the art are intended to be within the scope of the claims.

What is claimed is:

1. A tissue anchor apparatus, comprising:
  a first member defining one or more anchoring members having a length extending from a surface of the first member, each of the one or more anchoring members having a terminal piercing end and having mating features over at least a portion of the length;
  a second member defining one or more openings through which the one or more anchoring members are received in a corresponding manner; and,
  a third member defining one or more openings through which the one or more anchoring members are received, wherein the one or more openings defined by the third member comprises notches for engagement with the mating features defined on the first member to secure a position of the second member relative to the first member, wherein the third member is configured to be secured in position relative to the anchoring members and maintain a position of the second member relative to the first member, and wherein the second member has geometry which prevents engaging elements of the third member from flexing towards the first member.

2. The apparatus of claim 1 wherein the first and second members have shorter secondary piercing elements.

3. The apparatus of claim 1 wherein the one or more openings defined by the third member comprises a threaded opening for engaging upon the features over the portion of the length.

4. The apparatus of claim 3 wherein the second member and third member have mating features which allow the parts to be screwed together but resist unscrewing.

5. The apparatus of claim 1 wherein the second member further comprises ratchet fingers configured to engage with the features on the one or more anchoring members of the first member to maintain a position of the second member relative to the first member until engagement by the third member.

6. The apparatus of claim 1 wherein the third member further comprises one or more spring elements which couple to the one or more anchoring members of the first member while limiting motion of the second member relative to the first member.

7. The apparatus of claim 1 further comprising one or more pins for insertion through one or more channels defined orthogonally through the one or more anchoring members.

8. The apparatus of claim 7 wherein the one or more pins are connected to one another to simultaneously engage with the one or more channels.

9. The apparatus of claim 7 wherein the one or more pins comprise a retaining feature.

10. The apparatus of claim 7 wherein the second member defines a feature which inhibits disengagement of the pin from the channel.

11. A tissue anchoring assembly, comprising:
a first member having one or more first piercing elements extending from a first surface configured for contact against a first tissue region;
a second member configured for contact against a second tissue region, wherein the second member defines one or more openings corresponding to a position of the one or more first piercing elements, and wherein the first member and second member are configured to be secured relative to one another via the one or more first piercing elements;
a magnetically attractive element attachable to the first member and/or the second member;
a connecting element configured to be secured to the tissue anchoring assembly, wherein the magnetically attractive element is attachable to the connecting element;
a second magnetically attractive element positionable to apply an approximating force upon the magnetically attractive element;
a second tissue anchoring assembly attachable to the tissue anchoring assembly;
a second connecting element having a second magnetically attractive element attached thereto, wherein the second connecting element is configured to be secured to the second tissue anchoring assembly; and
a first external magnet which is adjustably engageable with the magnetically attractive element and a second external magnet which is adjustably engageable with the second magnetically attractive element.

12. The assembly of claim 11 further comprising a biasing element which adjustably couples the first and second external magnets to one another.

13. A tissue anchor apparatus, comprising:
a first member defining one or more anchoring members having a length extending from a surface of the first member, each of the one or more anchoring members having a terminal piercing end and having features over at least a portion of the length;
a second member defining one or more openings through which the one or more anchoring members are received in a corresponding manner; and,
a third member defining one or more openings through which the one or more anchoring members are received, wherein the one or more openings defined by the third member comprises a threaded opening for engaging upon the features over the portion of the length, wherein the third member is configured to be secured in position relative to the anchoring members and maintain a position of the second member relative to the first member, and wherein the second member and third member have mating features which allow the parts to be screwed together but resist unscrewing.

14. The apparatus of claim 13 wherein the first and second members have shorter secondary piercing elements.

15. The apparatus of claim 13 wherein the one or more openings defined by the third member comprises notches for engagement with mating features defined on the first member to secure a position of the second member relative to the first member.

16. The apparatus of claim 15 wherein the second member has geometry which prevents engaging elements of the third member from flexing towards the first member.

17. The apparatus of claim 13 wherein the second member further comprises ratchet fingers configured to engage with the features on the one or more anchoring members of the first member to maintain a position of the second member relative to the first member until engagement by the third member.

18. The apparatus of claim 13 wherein the third member further comprises one or more spring elements which couple to the one or more anchoring members of the first member while limiting motion of the second member relative to the first member.

19. The apparatus of claim 13 further comprising one or more pins for insertion through one or more channels defined orthogonally through the one or more anchoring members.

20. The apparatus of claim 19 wherein the one or more pins are connected to one another to simultaneously engage with the one or more channels.

21. The apparatus of claim 19 wherein the one or more pins comprise a retaining feature.

22. The apparatus of claim 19 wherein the second member defines a feature which inhibits disengagement of the pin from the channel.

23. A tissue anchor apparatus, comprising:
a first member defining one or more anchoring members having a length extending from a surface of the first member, each of the one or more anchoring members having a terminal piercing end and having features over at least a portion of the length;
a second member defining one or more openings through which the one or more anchoring members are received in a corresponding manner;
a third member defining one or more openings through which the one or more anchoring members are received, wherein the third member is configured to be secured in position relative to the anchoring members and maintain a position of the second member relative to the first member; and
one or more pins for insertion through one or more channels defined orthogonally through the one or more anchoring members, wherein the second member defines a feature which inhibits disengagement of the one or more pins from the one or more channels.

24. The apparatus of claim 23 wherein the first and second members have shorter secondary piercing elements.

25. The apparatus of claim 23 wherein the one or more openings defined by the third member comprises a threaded opening for engaging upon the features over the portion of the length.

26. The apparatus of claim 25 wherein the second member and third member have mating features which allow the parts to be screwed together but resist unscrewing.

27. The apparatus of claim 23 wherein the one or more openings defined by the third member comprises notches for engagement with mating features defined on the first member to secure a position of the second member relative to the first member.

28. The apparatus of claim 27 wherein the second member has geometry which prevents engaging elements of the third member from flexing towards the first member.

29. The apparatus of claim 23 wherein the second member further comprises ratchet fingers configured to engage with the features on the one or more anchoring members of the first member to maintain a position of the second member relative to the first member until engagement by the third member.

30. The apparatus of claim 23 wherein the third member further comprises one or more spring elements which couple to the one or more anchoring members of the first member while limiting motion of the second member relative to the first member.

31. The apparatus of claim 23 wherein the one or more pins are connected to one another to simultaneously engage with the one or more channels.

32. The apparatus of claim 23 wherein the one or more pins comprise a retaining feature.

33. A tissue anchor apparatus, comprising:
   a first member defining one or more anchoring members having a length extending from a surface of the first member, each of the one or more anchoring members having a terminal piercing end and having features over at least a portion of the length;
   a second member defining one or more openings through which the one or more anchoring members are received in a corresponding manner;
   a third member defining one or more openings through which the one or more anchoring members are received, wherein the third member is configured to be secured in position relative to the anchoring members and maintain a position of the second member relative to the first
   one or more pins having a retaining feature for insertion through one or more channels defined through the one or more anchoring members, wherein the second member defines a feature which inhibits disengagement of the one or more pins from the one or more channels.

34. The apparatus of claim 33 wherein the one or more channels are defined orthogonally through the anchoring member.

35. The apparatus of claim 33 wherein the one or more pins are connected to one another to simultaneously engage with the one or more channels.

* * * * *